United States Patent
Ben-Eliyahu et al.

(10) Patent No.: US 9,463,198 B2
(45) Date of Patent: Oct. 11, 2016

(54) COMPOSITIONS AND METHODS FOR REDUCING OR PREVENTING METASTASIS

(71) Applicant: Infectious Disease Research Institute, Seattle, WA (US)

(72) Inventors: Shamgar Ben-Eliyahu, Tel Aviv (IL); Pini Matzner, Netanya (IL); Steven G. Reed, Bellevue, WA (US)

(73) Assignee: Infectious Disease Research Institute, Seattle, WA (US)

( * ) Notice: Subject to any disclaimer, the term of this patent is extended or adjusted under 35 U.S.C. 154(b) by 0 days.

(21) Appl. No.: 14/256,881

(22) Filed: Apr. 18, 2014

(65) Prior Publication Data

US 2015/0087615 A1   Mar. 26, 2015

Related U.S. Application Data

(60) Provisional application No. 61/830,675, filed on Jun. 4, 2013.

(51) Int. Cl.
| | |
|---|---|
| *A01N 43/04* | (2006.01) |
| *A61K 31/715* | (2006.01) |
| *A61K 31/7024* | (2006.01) |
| *A61K 31/7008* | (2006.01) |
| *A61K 31/7016* | (2006.01) |
| *A61K 31/7012* | (2006.01) |
| *A61K 31/138* | (2006.01) |
| *A61K 31/407* | (2006.01) |
| *A61K 45/06* | (2006.01) |

(52) U.S. Cl.
CPC ......... *A61K 31/7024* (2013.01); *A61K 31/138* (2013.01); *A61K 31/407* (2013.01); *A61K 31/7008* (2013.01); *A61K 31/7012* (2013.01); *A61K 31/7016* (2013.01); *A61K 45/06* (2013.01)

(58) Field of Classification Search
None
See application file for complete search history.

(56) References Cited

U.S. PATENT DOCUMENTS

| | | |
|---|---|---|
| 3,238,190 A | 3/1966 | Erbring et al. |
| 3,598,122 A | 8/1971 | Zaffaroni |
| 3,598,123 A | 8/1971 | Zaffaroni |
| 4,029,762 A | 6/1977 | Galanos et al. |
| 4,286,592 A | 9/1981 | Chandrasekaran |
| 4,314,557 A | 2/1982 | Chandrasekaran |
| 4,379,454 A | 4/1983 | Campbell et al. |
| 4,420,461 A | 12/1983 | Reckel et al. |
| 4,420,558 A | 12/1983 | De Mey et al. |
| 4,435,386 A | 3/1984 | Ribi et al. |
| 4,436,728 A | 3/1984 | Ribi et al. |
| 4,568,343 A | 2/1986 | Leeper et al. |
| 4,595,654 A | 6/1986 | Reckel et al. |
| 4,614,722 A | 9/1986 | Pasula |
| 4,629,722 A | 12/1986 | Ribi |
| 4,659,659 A | 4/1987 | Dwek et al. |
| 4,663,306 A | 5/1987 | Cantrell |
| 4,743,540 A | 5/1988 | Ralph et al. |
| 4,767,402 A | 8/1988 | Kost et al. |
| 4,769,330 A | 9/1988 | Paoletti et al. |
| 4,780,212 A | 10/1988 | Kost et al. |
| 4,844,894 A | 7/1989 | Ribi |
| 4,897,268 A | 1/1990 | Tice et al. |
| 4,912,094 A | 3/1990 | Myers et al. |
| 4,948,587 A | 8/1990 | Kost et al. |
| 4,981,684 A | 1/1991 | MacKenzie et al. |
| 4,987,237 A | 1/1991 | Myers et al. |
| 5,017,487 A | 5/1991 | Stunnenberg et al. |
| 5,057,540 A | 10/1991 | Kensil et al. |
| 5,066,794 A | 11/1991 | Shiba |
| 5,075,109 A | 12/1991 | Tice et al. |
| 5,124,141 A | 6/1992 | Makler |
| 5,147,785 A | 9/1992 | Pasula |
| 5,162,990 A | 11/1992 | Odeyale et al. |
| 5,231,168 A | 7/1993 | Dziegiel et al. |
| 5,278,302 A | 1/1994 | Caruthers et al. |
| 5,298,396 A | 3/1994 | Kotzin et al. |
| 5,411,865 A | 5/1995 | Reed |
| 5,422,109 A | 6/1995 | Brancq et al. |
| 5,424,067 A | 6/1995 | Brancq et al. |
| 5,457,041 A | 10/1995 | Ginaven et al. |
| 5,464,387 A | 11/1995 | Haak et al. |

(Continued)

FOREIGN PATENT DOCUMENTS

| | | |
|---|---|---|
| DE | 3833319 A1 | 4/1989 |
| EP | 0109942 B1 | 5/1984 |

(Continued)

OTHER PUBLICATIONS

Coler et al. PLoS One (2011), vol. 6, Issue 1, e16333, pp. 1-12.*
Hahn et al. Int. J. Cancer (2006), vol. 118, pp. 2220-2231.*
Benish et al. Annals of Surgical Oncology (2008), vol. 15, pp. 2042-2052.*
Avraham, R. et al. (Aug. 2010, e-published Mar. 31, 2010). "Synergism Between Immunostimulation and Prevention of Surgery-Induced Immune Suppression: an Approach to Reduce Post-Operative Tumor Progression," *Brain, Behavior, Immunity* 24(6):952-958.
CAS Registry No. 525-66-6, STN Entry Date Nov. 16, 1984, 2-Propanol, 1-[(1-methylethyl)amino]-3-(1-naphthalenyloxy)-, 1 page.

(Continued)

*Primary Examiner* — Patrick Lewis
(74) *Attorney, Agent, or Firm* — Marshall, Gerstein & Borun LLP

(57) ABSTRACT

Compositions comprising glucopyranosyl lipid adjuvant (GLA) and methods for reducing or preventing the formation of cancer metastasis utilizing same are provided. The compositions may be formulated for local-regional delivery. The compositions may be substantially devoid of a cancer antigen. The treatment with GLA may be combined with treatment with a COX2 inhibitor and a beta-adrenergic blocker.

22 Claims, 4 Drawing Sheets

(56) References Cited

U.S. PATENT DOCUMENTS

| | | |
|---|---|---|
| 5,530,113 A | 6/1996 | Christ et al. |
| 5,565,209 A | 10/1996 | Rijke |
| 5,591,139 A | 1/1997 | Lin et al. |
| 5,595,888 A | 1/1997 | Gray et al. |
| 5,612,041 A | 3/1997 | Burke et al. |
| 5,612,476 A | 3/1997 | Christ et al. |
| 5,618,275 A | 4/1997 | Bock |
| 5,650,155 A | 7/1997 | Cornelius et al. |
| 5,654,140 A | 8/1997 | Persico et al. |
| 5,656,016 A | 8/1997 | Ogden |
| 5,666,153 A | 9/1997 | Copeland |
| 5,667,784 A | 9/1997 | Cornelius et al. |
| 5,693,531 A | 12/1997 | Chiorini et al. |
| 5,718,904 A | 2/1998 | Hjorth |
| 5,719,263 A | 2/1998 | Reed |
| 5,722,397 A | 3/1998 | Eppstein |
| 5,756,718 A | 5/1998 | Christ et al. |
| 5,776,468 A | 7/1998 | Hauser et al. |
| 5,786,148 A | 7/1998 | Bandman et al. |
| 5,795,577 A | 8/1998 | Kieny et al. |
| 5,840,871 A | 11/1998 | Hillman et al. |
| 5,843,464 A | 12/1998 | Bakaletz et al. |
| 5,843,918 A | 12/1998 | Christ et al. |
| 5,846,758 A | 12/1998 | Medenica |
| 5,885,211 A | 3/1999 | Eppstein et al. |
| 5,888,519 A | 3/1999 | Alving |
| 5,912,166 A | 6/1999 | Reed et al. |
| 5,952,309 A | 9/1999 | Rossignol et al. |
| 5,955,306 A | 9/1999 | Gimeno et al. |
| 5,961,970 A | 10/1999 | Lowell et al. |
| 5,976,538 A | 11/1999 | Hilgers et al. |
| 5,981,215 A | 11/1999 | Meissner et al. |
| 5,993,800 A | 11/1999 | Linsley et al. |
| 6,005,099 A | 12/1999 | Davies et al. |
| 6,018,678 A | 1/2000 | Mitragotri et al. |
| 6,027,730 A | 2/2000 | Francotte et al. |
| 6,027,732 A | 2/2000 | Morein et al. |
| 6,033,928 A | 3/2000 | Eriguchi et al. |
| 6,057,427 A | 5/2000 | Smith et al. |
| 6,106,824 A | 8/2000 | Kaplitt et al. |
| 6,120,769 A | 9/2000 | Gefter et al. |
| 6,146,632 A | 11/2000 | Momin et al. |
| 6,212,102 B1 | 4/2001 | Georgakos et al. |
| 6,218,186 B1 | 4/2001 | Choi et al. |
| 6,231,861 B1 | 5/2001 | Barnwell |
| 6,235,724 B1 | 5/2001 | Asai et al. |
| 6,261,762 B1 | 7/2001 | Alizon et al. |
| 6,270,769 B1 | 8/2001 | Raychaudhuri et al. |
| 6,309,847 B1 | 10/2001 | Cohen et al. |
| 6,316,183 B1 | 11/2001 | Alizon et al. |
| 6,322,532 B1 | 11/2001 | D'Sa et al. |
| 6,375,944 B1 | 4/2002 | Trinchieri et al. |
| 6,472,515 B1 | 10/2002 | Climent-Johansson et al. |
| 6,488,936 B1 | 12/2002 | Mishkin et al. |
| 6,491,919 B2 | 12/2002 | Crane |
| 6,512,102 B1 | 1/2003 | Xu et al. |
| 6,544,518 B1 | 4/2003 | Friede et al. |
| 6,544,728 B1 | 4/2003 | Alizon et al. |
| 6,555,653 B2 | 4/2003 | Alderson et al. |
| 6,572,861 B1 | 6/2003 | Roberts et al. |
| 6,587,792 B1 | 7/2003 | Thomas |
| 6,596,501 B2 | 7/2003 | Roth |
| 6,613,892 B2 | 9/2003 | Preston et al. |
| 6,630,161 B1 | 10/2003 | Leesman |
| 6,654,462 B1 | 11/2003 | Hedberg |
| 6,660,487 B2 | 12/2003 | Faustman |
| 6,676,961 B1 | 1/2004 | Lichter |
| 6,682,901 B2 | 1/2004 | Blaschuk et al. |
| 6,683,063 B2 | 1/2004 | Rossignol et al. |
| 6,685,699 B1 | 2/2004 | Eppstein et al. |
| 6,692,752 B1 | 2/2004 | Slaoui et al. |
| 6,706,872 B1 | 3/2004 | Barnwell |
| 6,713,068 B1 | 3/2004 | Audonnet et al. |
| 6,733,763 B2 | 5/2004 | Raychaudhuri et al. |
| 6,734,172 B2 | 5/2004 | Scholler et al. |
| 6,749,856 B1 | 6/2004 | Berzofsky et al. |
| 6,752,995 B2 | 6/2004 | Johnston et al. |
| 6,770,445 B1 | 8/2004 | Scholler et al. |
| 6,783,981 B1 | 8/2004 | Uden et al. |
| 6,797,276 B1 | 9/2004 | Glenn et al. |
| 6,828,155 B1 | 12/2004 | Kaneko et al. |
| 6,844,192 B2 | 1/2005 | Orlando et al. |
| 6,846,489 B1 | 1/2005 | Garcon et al. |
| 6,846,648 B2 | 1/2005 | Maes |
| 6,855,322 B2 | 2/2005 | Lyon et al. |
| 6,869,607 B1 | 3/2005 | Buschle et al. |
| 6,871,477 B1 | 3/2005 | Tucker |
| 6,875,610 B2 | 4/2005 | Higginbotham et al. |
| 6,893,820 B1 | 5/2005 | Plass |
| 6,908,453 B2 | 6/2005 | Fleming et al. |
| 6,911,434 B2 | 6/2005 | Baldridge et al. |
| 6,919,078 B2 | 7/2005 | Ni et al. |
| 6,919,210 B1 | 7/2005 | Okamoto |
| 6,929,796 B1 | 8/2005 | Conti-Fine |
| 6,932,972 B2 | 8/2005 | Stephenne et al. |
| 6,933,123 B2 | 8/2005 | Hu et al. |
| 6,936,255 B1 | 8/2005 | Wettendorff |
| 6,949,246 B2 | 9/2005 | Reed et al. |
| 6,969,704 B1 | 11/2005 | Pinsky et al. |
| 6,970,739 B1 | 11/2005 | Inoue |
| 6,974,588 B1 | 12/2005 | Miranda et al. |
| 6,977,073 B1 | 12/2005 | Cezayirli et al. |
| 6,979,535 B2 | 12/2005 | Alizon et al. |
| 6,979,730 B2 | 12/2005 | Reiter et al. |
| 6,991,791 B2 | 1/2006 | Le et al. |
| 7,001,770 B1 | 2/2006 | Atencio et al. |
| 7,008,774 B2 | 3/2006 | Ryan et al. |
| 7,012,134 B2 | 3/2006 | Ruben et al. |
| 7,018,345 B2 | 3/2006 | Mori et al. |
| 7,029,678 B2 | 4/2006 | Momin et al. |
| 7,029,685 B2 | 4/2006 | Lanar et al. |
| 7,030,232 B1 | 4/2006 | Reiter et al. |
| 7,033,598 B2 | 4/2006 | Lerner |
| 7,037,712 B2 | 5/2006 | Both et al. |
| 7,052,904 B2 | 5/2006 | Zheng et al. |
| 7,060,276 B2 | 6/2006 | Lanar et al. |
| 7,060,802 B1 | 6/2006 | Trakht et al. |
| 7,067,310 B2 | 6/2006 | Chartier et al. |
| 7,070,931 B2 | 7/2006 | Fujinaga et al. |
| 7,078,180 B2 | 7/2006 | Genetta |
| 7,084,256 B2 | 8/2006 | McCormick et al. |
| 7,087,231 B2 | 8/2006 | Guerin-Marchand et al. |
| 7,087,713 B2 | 8/2006 | Campos-Neto et al. |
| 7,357,936 B1 | 4/2008 | Garcon |
| 7,820,627 B2 | 10/2010 | Jiang et al. |
| 8,273,361 B2 | 9/2012 | Reed et al. |
| 8,343,512 B2 | 1/2013 | Reed et al. |
| 8,609,114 B2 | 12/2013 | Reed et al. |
| 8,722,064 B2 | 5/2014 | Reed et al. |
| 8,957,047 B2 | 2/2015 | Paya Cuenca et al. |
| 8,962,593 B2 | 2/2015 | Paya Cuenca et al. |
| 2002/0176867 A1 | 11/2002 | Andersen et al. |
| 2003/0165512 A1 | 9/2003 | Wheeler et al. |
| 2003/0170249 A1 | 9/2003 | Hakomori et al. |
| 2003/0194391 A1 | 10/2003 | Ashman et al. |
| 2003/0215497 A1 | 11/2003 | Leesman |
| 2004/0120924 A1 | 6/2004 | Hone et al. |
| 2004/0161776 A1 | 8/2004 | Maddon et al. |
| 2005/0123550 A1 | 6/2005 | Laurent et al. |
| 2007/0072824 A1 | 3/2007 | Kawano et al. |
| 2008/0131466 A1 | 6/2008 | Reed et al. |
| 2009/0181078 A1 | 7/2009 | Reed et al. |
| 2010/0310602 A1 | 12/2010 | Reed et al. |
| 2011/0014274 A1 | 1/2011 | Reed et al. |
| 2011/0070290 A1 | 3/2011 | Reed et al. |
| 2012/0039994 A1* | 2/2012 | Reed et al. .......... 424/450 |
| 2013/0084307 A1 | 4/2013 | Reed et al. |
| 2014/0037691 A1 | 2/2014 | Reed et al. |
| 2014/0193459 A1 | 7/2014 | Reed et al. |

(56) References Cited

U.S. PATENT DOCUMENTS

| | | | |
|---|---|---|---|
| 2014/0322268 A1 | 10/2014 | Reed et al. | |
| 2014/0341970 A1 | 11/2014 | Reed et al. | |

FOREIGN PATENT DOCUMENTS

| | | |
|---|---|---|
| EP | 0198474 A1 | 10/1986 |
| EP | 0224260 A2 | 6/1987 |
| EP | 0304578 A1 | 3/1989 |
| EP | 0324455 A2 | 7/1989 |
| EP | 0362279 A1 | 4/1990 |
| EP | 0366412 A2 | 5/1990 |
| EP | 0382271 A1 | 8/1990 |
| EP | 0414374 A2 | 2/1991 |
| EP | 0468520 A2 | 1/1992 |
| EP | 0 382 271 B1 | 12/1994 |
| EP | 0729473 A1 | 9/1996 |
| EP | 0761231 A1 | 3/1997 |
| EP | 1531158 A1 | 5/2005 |
| EP | 2068918 B1 | 5/2012 |
| GB | 2220211 A | 1/1990 |
| GB | 2232892 A | 1/1991 |
| JP | 63010728 A | 1/1988 |
| JP | 07055906 A | 3/1995 |
| JP | 10131046 A | 5/1998 |
| WO | WO-89/01973 A2 | 3/1989 |
| WO | WO-90/01496 A1 | 2/1990 |
| WO | WO-90/06951 A1 | 6/1990 |
| WO | WO-90/07936 A1 | 7/1990 |
| WO | WO-91/00106 A1 | 1/1991 |
| WO | WO-91/00107 A1 | 1/1991 |
| WO | WO-91/02805 A2 | 3/1991 |
| WO | WO-93/02184 A1 | 2/1993 |
| WO | WO-93/10152 A1 | 5/1993 |
| WO | WO-93/12778 A1 | 7/1993 |
| WO | WO-93/25234 A1 | 12/1993 |
| WO | WO-93/25698 A1 | 12/1993 |
| WO | WO-94/00152 A1 | 1/1994 |
| WO | WO-94/00153 A1 | 1/1994 |
| WO | WO-94/03622 A1 | 2/1994 |
| WO | WO-94/05792 A1 | 3/1994 |
| WO | WO-94/20137 A1 | 9/1994 |
| WO | WO-94/21292 A1 | 9/1994 |
| WO | WO-95/14026 A1 | 5/1995 |
| WO | WO-95/17209 A1 | 6/1995 |
| WO | WO-95/17210 A1 | 6/1995 |
| WO | WO-95/20600 A1 | 8/1995 |
| WO | WO-95/26204 A1 | 10/1995 |
| WO | WO-96/02555 A1 | 2/1996 |
| WO | WO-96/09310 A1 | 3/1996 |
| WO | WO-96/11272 A2 | 4/1996 |
| WO | WO-96/11711 A1 | 4/1996 |
| WO | WO-96/26277 A1 | 8/1996 |
| WO | WO-96/33739 A1 | 10/1996 |
| WO | WO-97/11708 A1 | 4/1997 |
| WO | WO-97/42947 A1 | 11/1997 |
| WO | WO-98/01139 A1 | 1/1998 |
| WO | WO-98/12302 A1 | 3/1998 |
| WO | WO-98/16247 A1 | 4/1998 |
| WO | WO-98/20117 A1 | 5/1998 |
| WO | WO-98/37418 A2 | 8/1998 |
| WO | WO-98/43670 A2 | 10/1998 |
| WO | WO-98/56414 A1 | 12/1998 |
| WO | WO-98/58956 A2 | 12/1998 |
| WO | WO-99/03884 A2 | 1/1999 |
| WO | WO-99/10375 A2 | 3/1999 |
| WO | WO-99/11241 A1 | 3/1999 |
| WO | WO-99/12565 A1 | 3/1999 |
| WO | WO-99/17741 A1 | 4/1999 |
| WO | WO-99/28475 A2 | 6/1999 |
| WO | WO-99/40188 A2 | 8/1999 |
| WO | WO-99/51748 A2 | 10/1999 |
| WO | WO-99/53061 A2 | 10/1999 |
| WO | WO-00/04149 A2 | 1/2000 |
| WO | WO-00/13029 A1 | 3/2000 |
| WO | WO-00/18929 A2 | 4/2000 |
| WO | WO-00/25815 A1 | 5/2000 |
| WO | WO-00/42994 A2 | 7/2000 |
| WO | WO-01/36433 A2 | 5/2001 |
| WO | WO-01/90129 A2 | 11/2001 |
| WO | WO-02/16560 A1 | 2/2002 |
| WO | WO-02/28424 A2 | 4/2002 |
| WO | WO-02/32450 A2 | 4/2002 |
| WO | WO-02/32454 A1 | 4/2002 |
| WO | WO-03/094850 A2 | 11/2003 |
| WO | WO-2006/055729 A1 | 5/2006 |
| WO | WO-2008/153541 A1 | 12/2008 |
| WO | WO-2009/035528 A2 | 3/2009 |
| WO | WO-2009/143457 A2 | 11/2009 |
| WO | WO-2010/141861 A1 | 12/2010 |
| WO | WO-2012/009611 A2 | 1/2012 |
| WO | WO-2013/119856 A1 | 8/2013 |
| WO | WO-2014/197629 A1 | 12/2014 |

OTHER PUBLICATIONS

CAS Registry No. 41340-25-4, STN Entry Date Nov. 16, 1984, Pyrano[3,4-b]indole-1-acetic acid, 1,8-diethyl-1,3,4,9-tetrahydro-, 2 pages.

International Search Report mailed on Oct. 2, 2014, for PCT Application No. PCT/US2014/040954, filed on Jun. 4, 2014, 3 pages.

Neeman, E. et al. (Sep. 15, 2012, e-published Jul. 2, 2012). "A New Approach to Reducing Postsurgical Cancer Recurrence: Perioperative Targeting of Catecholamines and Prostaglandins," *Clinical Cancer Research* 18(18):4895-4902.

Written Opinion mailed on Oct. 2, 2014, for PCT Application No. PCT/US2014/040954, filed on Jun. 4, 2014, 5 pages.

Ahmed et al., Links between toll-like receptor 4 and breast cancer, *OncoImmunol.* 2(2): e22945-1-e22945-7 (2013).

Akamatsu et al., Synthesis of lipid A monosaccharide analogues containing acidic amino acid: Exploring the structural basis for the endotoxic and antagonistic activities, *Bioorg. Med. Chem.*, 14:6759-77 (2006).

Akamizu et al., molecular analysis of stimulatory anti-thyrotropin receptor antibodies (TSAbs) involved in Graves' Disease, *J. Immunol.*, 157(7):3148-52 (1996).

Alexander et al., Bacterial lipopolysaccharides and innate immunity, *J. Endotoxin Res.*, 7(3):167-202 (2001).

Alving et al., Lipid A and liposomes containing lipid A as antigens and adjuvants, *Vaccine*, 26:3036-45 (2008).

Alving, Lipopolysaccharide, Lipid A, and Liposomes Containing Lipid A as Immunologic Adjuvants, *Immunobiol.*, 187:430-46 (1993).

American Thoracic Society, Standards for the diagnosis and care of patients with Chronic Obstructive Pulmonary Disease, *Am. J. Respir. Crit. Care Med.*, 152(5 Pt 2):577-5121 (1995).

Amos et al., Adoptive immunotherapy combined with intratumoral TLR agonist delivery eradicates established melanoma in mice. *Cancer Immunol. Immunother.* 60(5): 671-83 (2011).

Andaloussi et al., Stimulation of TLR9 with CpG ODN enhances apoptosis of glioma and prolongs the survival of mice with experimental brain tumors, *Glia*, 54(6):526-35 (2006).

Anderson et al., Physicochemical characterization and biological activity of synthetic TLR4 agonist formulations, *Colloids and Surfaces Biointerfaces*, 75(1):130 (2010).

Apicella et al., Antigenic heterogeneity of lipid A of Haemophilus imfluenzae, *Infect. Immun.*, 50:9-14 (1985).

Armant et al., Toll-like Receptors: a family of pattern-recognition receptors in mammals, *Genome Biol.*, 3(8):3011.1-.6 (2002).

Asai, Development of an injectable formulation for the novel Lipid A analog E5531 using a 'pH-jump method, *Yakugaku Zasshi*, 24(12):965-72 (2004).

Avanti Polar Lipids, Certificate of Analysis #770030—Monophosphoryl Lipid A (Synthetic cGMP) Dated Jan. 15, 2008.

Avanti Polar Lipids, Inc., Product Data Sheet for Avanti Product No. 699200, Lipid A—Purified Detoxified Lipid A, http://www.avantilipds.com, download date Jan. 14, 2009.

(56) References Cited

OTHER PUBLICATIONS

Avanti Polar Lipids, Inc., Product Data Sheet for Avanti Product No. 699800, Lipid(Synthetic)(PHAD™) Monophosphoryl Lipid A (Synthetic)(PHAD™) http://www.avantilipds.com, download date Jan. 14, 2009.
Avanti, Advertising: Synthetic Adjuvant, *J. Immunol.*, [Online] 178(10):1-5, May 15, 2007; XP002546530.
Avanti, Advertising: The New PHAD™ in vaccine technology Avanti's Synthetic Vaccine Adjuvant, J. Immunol., [Online] 179(12): 1-6, Dec. 15, 2007; XP002546531.
Avraham, et al., Synergism between immunostimulation and prevention of surgery-induced immune suppression: An approach to reduce postoperative tumor progression, *Brain Behav Immun.*, 24(6): 952-968 (Aug. 2010).
Azuma, et al., Development of immunoadjuvants for immunotherapy of cancer, *International* Immunopharmacology 1: 1249-1259 (2001).
Badaro et al., Evaluation of micro enzyme-linked Immunosorbent Assay (ELISA) for antibodies in American Visceral Leishmaniasis: antigen selection for detection of infection-specific responses, *Am. J. Trop. Med. Hyg.*, 35:72-8 (1986).
Badaro et al., rK39: A cloned antigen of Leishmania Chagasi that predicts active visceral leishmaniasis, *J. Infect. Dis.*, 173(3):758-61 (1996).
Bainbridge et al., Expression of a Porphyromonas gingivalis lipid A palmitylacyl transferase in *Escherichia coli* yields a chimeric lipid A with altered ability to stimulate interleukin-8 secretion, *Cell Microbiol.*, 8(1):120-9 (2006).
Baldridge et al., Monophosphoryl lipid A (MPL) formulations for the next generation of vaccines, *Methods*, 19:103-7 (1999).
Baldridge et al., Monophosphoryl lipid A enhances mucosol and systemic immunity to vaccine antigens following intranasal administration, *Vaccine*, 18:2416-25 (2000).
Baldridge et al., Taking a toll on human disease: Toll-like receptor 4 agonists as vaccine adjuvants and monotherapeutic agents, *Exp. Opin. Biol. Ther.*, 4(7): 1129-38 (2004).
Bardou et al., Antitumoral Effects of Lipids A, Clinical Studies, in Lipid A in Cancer Therapy, Chapter 11, pp. 125-31 (2009).
Bayes et al., Gateways to clinical trials, *Methods Exp. Clin. Pharmacol.*, 27(3):193-219 (2005).
Berkner, Development of adenovirus vectors for the expression of heterologous genes, *Biotechniques*, 6(7):616-27 (1988).
Bertholet et al., Optimized subunit vaccine protects against experimental leishmaniasis, *Vaccine*, 27(50):7036-45 (2009).
Bomford et al., Adjuvanticity and ISCOM formation by structurally diverse saponins, *Vaccine*, 10(9):572-7 (1992).
Borges et al., Potent stimulation of the innate immune system by a Leishmania brasiliensis recombinant protein, *Infect. Immun.*, 69(9):5270-7 (2001).
Bortolatto et al., Toll-Like receptor 4 agonists adsorbed to aluminum hydroxide adjuvant attenuate ovalbumin-specific allergic airway disease: Role of MyD88 adaptor molecule and interleukin-12/ interferon-y axis, Clin. Exper. Allergy, 38:1668-79 (2008).
Brade et al., Immunogenicity and antigenicity of synthetic *Escherichia coli* Lipid A, *Infect. Immunity*, 51(1):110-4 (1986).
Brade et al., The Immunogenicity and Antigenicity of Lipid A are influenced by its physicochemical state and environment, *Infect. Immunity*, 55(11):2636-44 (1987).
Brandenberg, Fourier transform infrared spectroscopy characterization of the lamellar and nonlamellar structures of free lipid A and Re lipopolysaccharides from *Salmonella minnesota* and *Escherichia coli*, *Bioohys. J.*, 64:1215-31 (1993).
Brandenburg et al., Conformational studies of synthetic lipid A analogues and partial structures by infrared spectroscopy, *Biochim. Biophys. Acta*, 1329:183-201 (1997).
Brandenburg et al., Endotoxins: relationships between structure, function, and activity, *Curr. Topics Med. Chem.* 4(11):1127-46 (2004).

Brandenburg et al., Physicochemical characteristics of triacyl lipid A partial structure OM-174 in relation to biological activity, *Eur. J. Biochem.*, 267:3370-7 (2000).
Bray et al., The immunology and serology of leishmaniasis. iv. result of ouchterlony double diffusion tests, *Trans. R. Soc. Trop. Med. Hyg.*, 60(5):605-9 (1966).
Brazolot et al., CpG DNA can induce strong Th1 humoral and cell mediated immune responses against hepatitis B surface antigen in young mice, *Proc. Natl. Acad. Sci. USA*, 95(26):15553-8 (1998).
Bulusu et al., Acyclic analogs of lipid A: synthesis and biological activities, *J. Med. Chem.*, 35(19):3463-9 (1992).
Burrell, Immunomodulation by bacterial endotoxin, *Microbiology*, 17(3):189-208 (1990).
Cady et al., Somnogenic activities of synthetic Lipid A, *Infect. Immunity*, 57(2):396-403 (1989).
Campagnari et al., Role of lipooligosaccharides in experimental dermal lesions caused by Haemophilus ducreyi, *Infect. Immun.*, 59:2601-8 (1991).
Casale et al., Safety of the intranasal toll-like receptor 4 agonist CRX-675 in allergic rhinitis, *Asthma Immunol.* 97(4):454-6 (2006).
Casella et al., Putting endotoxin to work for us: Monophosphoryl lipid A as a safe and effective vaccine adjuvant, *Cell Mol. Life Sci.*, 65:3231-40 (2008).
Chen et al., Distinct responses of lung and spleen dendritic cells to the TLR9 Against CpG oligodeoxynucleotide, *J. Immunol.*, 177(4):2373-83 (2006).
Choudhary et al., An Indirect Fluorescent Antibody (IFA) test for the serodiagnosis of Kala-Azar, *J. Comm. Dis.*, 24(1):32-6 (1992).
Choudhary et al., Enzyme-linked immunosorbent assay in the diagnosis of Kala-azar in Bhadohi (Varanasi), India, *Trans. R. Soc. Trop. Med. Hyg.*, 84(3):363-6 (1990).
Ciprandi et al., Emerging anti-inflammatory agents for allergic rhinitis, *Exp. Opin. Emerg. Drugs*, 10(4):689-705 (2005).
Coler et al., Immunization with a polyprotein vaccine consisting of the t-cell antigens thiol-specific antioxidant, leishmania major stress-inducible protein 1, and leishmania elongation initiation factor protects against leishmaniasis, *Infect. Immunity*, 70(8):4215-25 (2002).
Cooper et al., CPG 7909 Adjuvant improves Hepatitis B virus vaccine seroprotection in antiretroviral-treated HIV-infected adults, *AIDS*, 19(14):1473-9 (2005).
Correale et al., In vitro generation of human cytotoxic t lymphocytes specific for peptides derived from prostate-specific antigen, *J. National Cancer Institute*, 89(4):293-300 (1997).
Cotten et al., High-efficiency receptor-mediated delivery of small and large (48 Kilobase Gene Constructs Using the Endosome-Disruption Activity of Defective or Chemically Inactivated Adenovirus Particles), *Proc. Natl. Acad. Sci. USA*, 89(13):6094-8 (1992).
Curiel et al., High efficiency gene transfer mediated by adenovirus coupled to DNA-polylysine complexes, *Hum. Gene Ther.*, 3(2):147-54 (1992).
D'Agostini et al., Antitumor effect of OM-174 and cyclophosphamide on murine B16 melanoma in different experimental conditions. *Intl. Immunopharmacol.*, 5: 1205-12 (2005).
Darveau et al., Lipid A diversity and the innate host response to bacterial infection, *Curr. Opin. Microbiol.*, 1:36-42 (1998).
Datta et al., A Subset of Toll-Like Receptor ligands induces cross-presentation by bone marrow-derived dendritic cells, *J. Immunol.*, 170(8):4102-10 (2003).
Davis et al., CpG DNA is a potent enhancer of specific immunity in mice immunized with recombinant Hepatitis B surface antigen, *J. Immunol.*, 160(2):870-6 (1998).
Davis et al., Intratumoral administration of TLR4 agonist absorbed into a cellular vector improves antitumor responses. *Clin. Cancer Res.*, 17: 3984-92 (2011).
de Bono et al., Phase I study of ONO-4007, a synthetic analogue of the lipid A moiety of bacterial lipopolysaccharide, *Clin. Cancer Res.*, 6: 397-405 (2000).
Declaration of Dr. David T. Hickman submitted in support of opposition of European Patent No. EP-2068918 B1, dated Jan. 31, 2013.

(56) References Cited

OTHER PUBLICATIONS

Declaration of Dr. Maria Pilar Lopez-Deber submitted in support of opposition of European Patent No. EP-2068918 B1, dated Jan. 31, 2013.
Deng et al., CpG oligodeoxynucleotides stimulate protective innate immunity against pulmonary klebsiella infection, *J. Immunol.*, 173:5148-55 (2004).
Diks et al., LPS signal transduction: The picture is becoming more complex, *Curr. Topics Med. Chem.*, 4:1115-26 (2004).
Dixon et al., Lipopolysaccharide heterogeneity: Innate hos responses to bacterial modification of Lipid A structure, *J. Dent Res.*, 84(7):584-95 (2005).
Edelman, The development and use of vaccine adjuvants, *Mol. Biotechnol.*, 21(2):129-48 (2002).
Edelman, Vaccine adjuvants, *Rev. Infect. Dis.*, 2(3):370-83 (1980).
El-On et al., Leishmania Donovani: Physicochemical, immunological, and biological characterization of excreted factor from promastigotes, *Exper. Parasitol.*, 47(2):254-69 (1979).
European Application No. 07 875 082.5, Office Action mailed Feb. 2, 2010.
Fearon et al., The instructive role of innate immunity in the acquired immune response, *Science*, 272(5258):50-4 (1996).
Feigner et al., Lipofection: A highly efficient, lipid-mediated DNA-transfection procedure, *Proc. Natl. Acad. Sci. USA*, 84(21):7413-7 (1987).
Feuillet et al., Involvement of toll-like receptor 5 in the recognition of flagellated bacteria, *Proc. Natl. Acad. Sci. USA*, 103(33):12487-92 (2006).
Flad et al., Interleukin 1 and tumor necrosis factor: Studies on the induction by lipopolysaccharide partial structures, *Lymphokine Research*, 8(3): 235-8 (1989).
Flesher et al., Characterization of lipopolysaccharide of Haemophilus influenzae, *J. Infect. Dis.*, 138:719-30 (1978).
Fujimoto et al., Synthesis of lipid A and its analogues for investigation of the structural basis for their bioactivity, *J. Endotoxin Res.*, 11(6):341-7 (2005).
Funatogawa et al., Relationship of structure and biological activity of monosaccharide lipid A analogues to induction of nitric oxide production by murine macrophase RAW264.7 cells, *Infect. Immun.*, 5792-8 (1998).
Galanos et al., Endotoxic properties of chemically synthesized lipid A part structures, *Eur. J. Biochem.*, 140:221-7 (1984).
Galanos et al., Synthetic and natural *Escherichia coli* free lipid A express identical endotoxic activities, *Eur. J. Biochem.*, 148:1-5, (1985).
Garay et al., Cancer relapse under chemotherapy: Why TLR2/4 receptor agonists can help, *Europ. J. Pharmacol.*,563(1-3):1-17 (2007).
Garcon, Preclinical development of A504, *Methods in Molecular Biology*, 626:15-27 (2010).
Garidel et al., Divalent cations affect chain mobility and aggregate structure of lipopolysaccharide from *Salmonella minnesota* reflected in a decrease of its biological activity, *Biochim. Biophys. Acta*, 17:122-31 (2005).
Gatouillat et al., Immunization with liposome-anchored pegylated peptides modulates doxorubicin sensitivity in P-glycoprotein-expressing P388 cells, *Cancer Lett.*, 257: 165-71 (2007).
Gibson et al., Plasmacytoid dendritic cells produce cytokines and mature in response to the TLR7 agonists, imiquimod and resiquimod, *Cell. Immunol.*, 218(1-2):74-86 (2002).
Gisvold, Digitonin and phytosterol from the seed of digitalis purpurea, *Phytochem. Notes Amer. Pharmacol. Assoc.*, 23(7):664-6 (1934).
Glasner, et al., Improving Survival rates in two models of spontaneous postoperative metastasis in mice by combined administration of a ⊐-adrenergic antagonist and a cyclooxygenase-2 inhibitor, *J. Immunology*, 184: 2449-2457 (2010).
Gluck, Immunopotentiating Reconstituted Influenza Virosomes (IRIVs) and other adjuvants for improved presentation of small antigens, *Vaccine*, 10(13):915-9 (1992).
Goldman, Translational mini-review series on toll-like receptors: Toll-like receptor ligands as novel pharmaceuticals for allergic disorders, *Clin. Exper. Immunol.*, 147:208-16 (2007).
Gorden et al., Synthetic TLR agonists reveal functional differences between human TLR7 and TLR8, *J. Immunol.*, 174:1259-68 (2005).
Green et al., Mitochondria and apoptosis, *Science*, 281(5381):1309-12 (1998).
Griffiths et al., Studies toward Lipid A: Synthesis of differentially protected disaccharide fragments, *J. Org. Chem.*, 62(11):3654-8 (1997).
Gutsmann et al., Lipopolysaccharide-binding protein-mediated interaction of lipid A from different origin with phospholipid membranes, *Phys. Chem.*, 2:4521-8 (2000).
Hajjar et al., Human Toll-like receptor 4 recognizes host-specific LPS modifications, *Nat. Immunol.*, 3(4):354-9 (2002).
Hampton et al., Macrophage catabolism of lipid A is regulated by endotoxin stimulation, *J. Biol. Chem.*, 266(29):19499-509 (1991).
Harmey et al., Lipopolysaccharide-induced metastatic growth is associated with increased angiogenesis, vascular permeability and tumor cell invasion. *Int. J. Cancer*, 101: 415-22 (2002).
Hasegawa et al., Elevated promotion of prostacyclin production by synthetic lipid A analogs in aged human endothelial cells in culture, *Mech. Ageing Develop.*, 78:155-62 (1995).
Hawkins et al., A novel class of endotoxin receptor agonists with simplified structure, toll-like receptor 4-dependent immunostimulatory action, and adjuvant activity, *J. Pharmacol. Exper. Therap.*, 300(2):655-61 (2002).
Helander et al., Chemical structure of the lipopolysaccharide of Haemophilus influenzae strain I-69 Rd-/13+, *Eur. J. Biochem.*, 177:483-92 (1988).
Hemmi et al., Small anti-viral compounds activate immune cells via the TLR7 MyD88-dependent signaling pathway, *Nat. Immunol.*, 3(2):196-200 (2002).
Hilgers et al., Synergistic effects of synthetic adjuvants on the humoral immune response, *Mt. Archs. Allergy Appl. Immunol.*, 79(4):392-6 (1986).
Hilgers et al., Synthetic sulpholipopolysaccharides: novel adjuvants for humoral immune responses, *Immunology*, 60(1):141-6 (1987).
Homma et al., Structural Requirements of Lipid A Responsible for the Functions: A study with chemically synthesized lipid A and its analogues, *J. Biochem.*, 98(2):395-406 (1985).
Horsmans et al., Isatoribine, an agonist of TLR7, reduces plasma virus concentration in chronic Hepatitis C infection, *Hepatol.*, 42(3):724-31 (2005).
Hsiao et al., Toll-Like receptor-4 agonist inhibits motility and invasion of hepatoblastoma HepG2 cells in vitro, *Ped. Blood & Cancer*, 60(2):252 (2012).
Hubert et al., STEAP: A prostate-specific cell-surface antigen highly expressed in human prostate tumors, *Prot. Natl. Acad. Sci. USA*, 96(25):14523-8 (1999).
Imoto et al., Chemical synthesis of phosphorylated tetraacyl disaccharide corresponding to a biosynthetic precursor of Lipid A, *Tetrahedron Lett.*, 25(25):2667-70 (1984).
Imoto et al., Total synthesis of *Escherichia coli* lipid A, *Tetrahedron Lett.*, 26(12):1545-8 (1985).
Imoto et al., Total synthesis of *Escherichia coli* lipid A, the endotoxically active principle of the cell-surface lipopolysaccharide, *Bull. Chem. Soc. JP*, 60:2205-14 (1987).
Imoto et al., Total Synthesis of Lipid A, Active Principle of Bacterial Endotoxin, *Proc. Japan Acad.*, 60(B):285-8 (1984).
Invoices for the sale of PHAD™ from Avanti Polar Lipids, Inc. to AC Immune SA.
Isambert et al., Phase I study of OM-174, a lipid A analogue, with assessment of immunological response, in patients with refractory solid tumors. *BMC Cancer*, 13: 172-83 (2013).
Ishida et al., Regression of line-10 hepatocellular carcinoma by a less toxic cord factor analogue combined with L18-MDP or synthetic lipid A analogues. *Vaccine*, 6: 440-4 (1988).

(56) References Cited

OTHER PUBLICATIONS

Jacobson et al, Epidemiology and estimated population burden of selected autoimmune diseases in the United States, *Clin. Immunol. Immunopathol.*, 84(3):223-43 (1997).
Jiang et al., Lipid A structures containing novel lipid moieties: Synthesis and adjuvant properties, *Bioorg. Med. Chem. Lett.*, 12:2193-96 (2002).
Jiang et al., Monophosphoryl lipid A analogues with varying 3-O-substitution: synthesis and potent adjuvant activity, *Carbohydrate Research*, 342(6):784-96 (2007).
Jiang et al., Novel lipid A mimetics derived from pentaerythritol: synthesis and their potent agonistic activity, *Tetrahedron*, 58:8833-42 (2002).
Johansen et al., Toll-like receptor ligands as adjuvants in allergen-specific immunotherapy, Clin. Exp. Allerg., 35(12):1591-8 (2005).
Johnson et al., 3-0-Desacyl monophosphoryl Lipid A derivatives: Synthesis and immunostimulant activities, *J. Med. Chem.*, 42(22):4640-9 (1999).
Johnson et al., A comparison of the immunomodulating properties of two forms of monophosphoryl lipid A Analogues, *J. Immunother.*, 10:398-404 (1991).
Johnson et al., Chemical synthesis of the major constituents of *Salmonella minnesota* moniphosphoryl lipid A, *J. Carb. Chem.*, 7(9):1421-6 (1998).
Johnson et al., TLR4 agonists as vaccine adjuvants, *Vacc. Adjuv. Deliv. Syst.*, 131-56 (2007).
Johnson, Molecular adjuvants and immunomodulators: New approaches to immunization, *Clin. Microbiol. Rev.*, 7(3):277-89 (1994).
Jurgens et al., Interaction of hemoglobin with enterobacterial lipopolysaccharide and lipid A, *Eur. J. Biochem.*, 268:4233-42 (2001).
Kaisho et al., Pleiotropic function of toll-like receptors, *Microbes Infect.*, 6(15):1388-94 (2004).
Kanegasaki et al., Biological activities of analogues of lipid A based chemically on the revised structural model, *Eur. J. Biochem.*, 143(2):237-42 (1984).
Kanegasaki et al., Structure-activity relationship of lipid A: comparison of biological activities of natural and synthetic lipid A's with different fatty acid compositions, *J. Biochem.*, 99(4):1203-10 (1986).
Kanzler et al., Therapeutic targeting of innate immunity with Toll-like receptor agonists and antagonists, *Nature Medicine*, 13(5):552-9 (2007).
Kasai et al., Immunochemistry of lipid A, *Adv. Exp. Med. Biol.*, 256:71-9 (1990).
Kasai et al., In Vitro antigenic reactivity of synthetic lipid A analogues as determined by monoclonal and conventional antibodies, *Biochem. Biophys. Res. Commun.*, 128(2):607-12 (1985).
Kasai et al., Structure-activity relationships of endotoxic lipid A containing 2,3-diamino-2,3-dideoxy-D-glucose, in Cellular and Molecular Aspects of Endotoxin Reactions: Proceeding of the 1st congress of the international endotoxin society, Elsevier Science Publishers B.V. (Biomedical Division), San Diego, May 9-12, 121-8 (1990).
Kastenmuller et al., Full length Plasmodium falciparum Circumsporozite Protein Administered with Long-Chain Poly (IC) or the Toll-Like Receptor 4 Agonist Glucopyranosy Lipid Adjuvant-Stable Emulsion Elicits Potent Antibody and CD4+ T Cell Immunity and Protection in Mice, *Infection and Immunity*, 81(3):789-800 (2012).
Kawahara et al., Modification of the structure and activity of lipid A in Yersinia pestis lipopolysaccharide by growth temperature, *Infect. Immunity*, 70(8):4092-8 (2002).
Kelly et al., TLR-4 Signaling promotes tumor growth and paclitaxel chemoresistance in ovarian cancer, *Cancer Res.*, 66: 3859-68 (2006).
Kelly, et al., TLR-4 signaling promotes tumor growth and paclitaxel chemoresistance in ovarian cancer, *Cancer Research*; 66: 3859-3868 (2006).
Kelsh, et al., Topographical changes in extracellular matrix: activation of TLR4 signaling and solid tumor progression, *Trends Cancer Res.*, 9: 1-13 (Jan. 1, 2013).
Kensil et al., Separation and characterization of saponins with adjuvant activity from Quillaja Saponaria molina cortex, *J. Immunology*, 46(2):431-7 (1991).
Kensil, Saponins as vaccine adjuvants, *Crit. Rev. Ther. Drug Carrier Syst.*, 13(1-2):1-55 (1996).
Kersten et al., Liposomes and ISCOMs, *Vaccine*, 21:915-20 (2003).
Kim et al., Crystal Structure of the TLR4-MD-2 complex with bound endotoxin antagonist eritoran, *Cell*, 130:906-17 (2007).
Kiso et al., Synthesis of the Optically Active 4-0-phosphono-d-glucosamine derivatives related to the nonreducing-sugar subunit of bacterial lipid A, *Carbohyd. Res.*, 162:127-40 (1987).
Knirel et al., Conserved and variable structural features in the lipopolysaccharide of Pseudomonas aeruginosa, *J. Endotox. Res.*, 12(6):324-36 (2006).
Koido et al., The combination of TLR2 and TLR4 agonists promotes the immunogenicity of dendritic cell/cancer cell fusions, *Oncoimmunology*, 2(7):e24660-2 (2013).
Kolls et al., Prolonged and effective blockade of tumor necrosis factor activity through adenovirus-mediated gene transfer, *Proc. Natl. Acad. Sci. USA*, 91:215-9 (1994).
Kotani et al., Immunobiological activities of synthetic lipid A analogs with low endotoxicity, *Infect. Immunity*, 54(3): 673-8 (1986).
Kotani et al., Low endotoxic activities of synthetic salmonella-type lipid A with an additional acyloxyacyl Group on the 2-Amino group of beta(1-6)glucosamine disaccharide 1,4'-bisphosphate, *Infect. Immunity*, 52(3):872-84 (1986).
Kotani et al., Structural requirements of Lipid A Endotoxicity and other biological activities—An Overview, *Adv. Exp. Med. Biol.*, 256:13-43 (1990).
Kotani et al., Synthetic lipid A with endotoxic and related biological activities comparable to those of a natural lipid A from an *Escherichia coli* re-mutant, *Infect. Immunity*, 49(1):225-37 (1985).
Kukuoka et al., Structural characterization of lipid A component of Erwinia carotovora lipopolysaccharide. *Arch. Microbiol.* 157: 311-8 (1992).
Kumazawa et al., Importance of Fatty Acid Substituents of Chemically Synthesized Lipid A-Subunit analogs in the expression of immunopharmacological activity, *Infect. Immunity*, 56(1):149-55 (1988).
Kusumoto et al., Structural basis for endotoxic and antagonistic activities: investigation with novel synthetic lipid A analogs, *J. Endotox. Res.*, 9(6):361-6 (2003).
Kusumoto et al., Synthesis of endotoxic principle of bacterial lipopolysaccharide and its recognition by the innate immune systems of hosts, *Chem. Record*, 6:333-43 (2006).
Lacaille-Dubois et al., A review of the biological and pharmacological activities of saponins, *Phytomedicine*, 2(4):363-86 (1996).
Lee et al., Activation of anti-Hepatitis C virus responses via toll-like receptor 7, *Proc. Nat. Acad. Sci. USA*, 103(6):1828-33 (2006).
Letter from the Opponent, Opposition against EP 2068918, Opposition by Avanti Polar Lipids, Inc. dated Mar. 4, 2014.
Letter from Thomas G. Peterson to Steven G. Reed, Ph.D. dated Mar. 4, 2011.
Li et al., Assessment of recombinant adenoviral vectors for hepatic gene therapy, *Hum. Gene Ther.*, 4(4):403-9 (1993).
Lien et al., A novel synthetic acyclic lipid A-like agonist activates cells via the lipopolysaccharide/Toll-like Receptor 4 signaling pathway, *J. Biol. Chem.*, 276(3):1873-80 (2001).
Lien et al., Adjuvants and their signaling pathways: Beyond TLRs, *Nat. Immunol.*, 4(12):1162-4 (2003).
Life Sciences Discovery Fund Announces Grants to Commercialize Health-Related Products and Services, Jun. 27, 2013.
Lin et al., Implication of toll-like receptor and tumor necrosis factor alpha signaling in septic shock, *Shock*, 24(3):206-9 (2005).
Lin et al., In vitro and in vivo anticancer activity of a synthetic glycolipid as a toll-like receptor 4 (TLR4) activator, *J. Biol. Chem.*, 286(51):43782-92 (2011).
Liu et al., A divergent synthesis of lipid A and its chemically stable unnatural analogues, *Bull. Chem. Soc. Jpn.*, 72:1377-85 (1999).

(56) References Cited

OTHER PUBLICATIONS

Liu et al., Enzymatic preparation of (S)-3-Hydroxytetradecanoic acid and synthesis of unnatural analogues of lipid A containing the (S)-Acid, *Bull. Chem. Soc. Jpn.*, 70:1441-50 (1997).
Liu, Vaccine developments, *Nat. Med.*, 4(5):515-9 (1998).
Loppnow et al., Lipid A, The immunostimulatory principle of lipopolysaccharides?, *Adv. Exp. Med. Biol.*, 156:561-6 (1990).
Lu et al., A Novel Gene (PLU-1) containing highly conserved putative dna/chromatin binding motifs is specifically up-regulated in breast cancer, *J. Bio. Chem.*, 274(22):15633-45 (1999).
Luster, The role of chemokines in linking innate and adaptive immunity, *Curr. Opin. Immunol.*, 14(1):129-35 (2002).
Maeda et al., Adjuvant activities of synthetic lipid A subunit analogues and its conjugates with muramyl dipeptide derivatives, *Vaccine*, 7(3):275-81 (1989).
Mai et al., Should a toll-like receptor 4 (TLR-4) agonist or antagonist be designed to treat cancer? TLR-4: Its expression and effects in the ten most common cancers, *OncoTargets Ther.* 6: 1573-87 (2013).
Malakoff, Aluminum is put on trial as a vaccine booster, *Science*, 288(5470):1323-4 (2000).
Masoud et al., Investigation of the structure of lipid A from Actinobacillus actinomycetemcomitans strain Y4 and human clinical isolate PO 1021-7, *Eur. J. Biochem.*, 200:775-9 (1991).
Mata-Haro et al., The vaccine adjuvant monophosphoryl lipid A as a TRIF-biased agonist of TLR4, *Science*, 316:1628-2 (2007).
McCluskie et al., CpG DNA is a potent enhancer of systemic and mucosal immune responses against hepatitis B surface antigen with intranasal administration to Mice, *J. Immunol.*, 161(9):4463-6 (1998).
Medzhitov et al., Innate immunity: Impact on the adaptive immune response, *Curr. Opin. Immunol.*, 9(1):4-9 (1997).
Medzhitov, Toll-like receptors and innate immunity, *Nat. Rev. Immunol.*, 1(2):135-45 (2001).
Melaugh et al., Partial characterization of the major lipooligosaccharide from a strain of Haemophilus ducreyi, the causative agent of chancroid, a genital ulcer disease, *J. Biol. Chem.*, 267:13434-9 (1992).
Merck Index Online (SM), CAS Registry No. 11024-24-1, Digitonin, 2005.
Merck Index Online (SM), CAS Registry No. 111-02-4, Squalene, 2005.
Merck Index Online (SM), CAS Registry No. 6805-41-0, Escin, 2005.
Mikhail et al., Structural characterization of lipid A from nontypeable and type f Haemophilus influenzae: Variability of fatty acid substitution, *Analytical Biochem.*, 340:303-16 (2005).
Minutes of the MDR1 Teleconference, Jul. 26, 2005.
Mitchell et al., Expression of the pneumolysin gene in *Escherichia coli*: Rapid purification and biological properties, *Biochem. Biophys. Acta*, 1007:67-72 (1989).
Molavi et al., Immunomodulatory and anticancer effects of intratumoral co-delivery of synthetic lipid A adjuvant and STAT3 inhibitor, JSI-124, *Immunopharmacol. Immunotoxicol.*, 31(2): 214-21 (2009).
Moran, Biological and serological characterization of Campylobacter jejuni lipopolysaccharides with deviating core and lipid A structures, *FEMS Immunol. and Med. Microbiol.*, 11:121-30 (1995).
Mueller et al., Aggregates are the biologically active units of endotoxin, *J. Biol.Chem.*, 279(25):26307-313 (2004).
Muotiala, et al., Low biological activity of helicobacter pylori lipopolysaccharide, *Infect. Immunity*, 60(4):1714-16 (1992).
Myers et al., A critical determinant of lipid A endotoxic activity, Cellular and molecular aspects of endoxoix reactions, 145-56 (1990).
Nakao et al., Surface-expressed TLR6 participates in the recognition of diacylated lipopeptide and peptidoglycan in human cells, *J. Immunol.*, 174:1566-73 (2005).
Nakatsuka et al., Enhancement of nonspecific resistance to bacterial infections and tumor regressions by treatment with synthetic lipid A-subunit analogs. Critical role of N- and 3-O-linked acyl groups in 4-O-phophono-D-glucosamine derivatives, *Int. J. Immunopharmacol.* 11(4): 349-58 (1989)—Abstract only.
Nakatsuka et al., Inhibition in mice of experimental metastasis of B16 melanoma by the synthetic lipid A-subunit analogue GLA-60, *Int. J. Immunopharmacol.* 13(1): 11-19 (1991).
Naor, et al., Metastatic-promoting effects of LPS: sexual dimorphism and mediation by catecholamines and prostaglandins, *Brain, behavior, and Immunity*, 23; 611-621 (2009).
Nelson et al., Molecular cloning and characterization of prostase, an androgen-regulated serine protease with prostate-restricted expression, *Proc. Natl. Acad. Sci. USA*, 96(6):3114-9 (1999).
Notice of Opposition Against European Patent No. 2 068 912-B1 (European Application No. 07 87 5082.5), Vaccine Composition Containing Synthetic Adjuvant, 36 pages, dated Feb. 1, 2013.
Oblak et al., Toll-like receptor 4 activation in cancer progression and therapy, *Clin. Dev. Immunol.*, 2011: 609579 (2011).
Oblak, et al., Toll-like receptor 4 activation in cancer progression and therapy, *Clinical and Developmental Immunology*, vol. 2011, Article ID 609579, 1-12 (2011).
Pance et al., Antitumoral effects of lipid A: Preclinical and clinical studies, *J. Investig. Med.*, 50(3): 173-8 (2002).
PCT Application No. PCT/US2007/021017, International Filing Date Sep. 26, 2007, International Search Report and Written Opinion mailed Oct. 17, 2008.
PCT Application No. PCT/US2009/045033, International Filing Date May 22, 2009, International Search Report and Written Opinion mailed Mar. 9, 2010.
PCT Application No. PCT/US2010/37466, International Filing Date Jun. 4, 2010, International Search Report and Written Opinion mailed Aug. 25, 2010.
Persing et al., Taking Toll: Lipid A Mimetics as Adjuvants and Immunomodulators, *Trends in Microbiology*, 10(10):S32-7 (2002).
PHAD™ advertisement, *J. Biol. Chem.*, 282 (2007).
Piekarz et al., Epigenetic modifiers: Basic understanding and clinical development, *Clin. Cancer Res.*, 15: 3918-26 (2009).
Qureshi et al., Complete structural determination of lipopolysaccharide obtained from deep rough mutant of *Escherichia coli*, *J. Biol. Chem.*, 263:11971-6 (1988).
Qureshi et al., Monophosphoryl lipid A obtained from lipopolysaccharides of *Salmonella minnesota* R595, *J. Biol. Chem.*, 260(9):5271-8 (1985).
Qureshi et al., Position of ester groups in the lipid A backbone of lipopolysaccharides obtained from *Salmonella typhimurium*, *J. Biol. Chem.*, 258(21):12947-51 (1983).
Qureshi et al., Purification and structural determination of nontoxic lipid A obtained from the lipopolysaccharide of *Salmonella typhimurium*, *J. Biol. Chem.*, 257(19):11808-15 (1982).
Raetz et al., Kdo2-lipid A of *Escherichia coli*, a defined endotoxin that activates macrophages via TLR-4, *J. Lipid Res.*, 47:1097-111 (2006).
Reed et al., An improved serodiagnostic procedure for visceral leishmaniasis, *Am. J. Trop. Med. Hyg.*, 43(6):632-9 (1990).
Reed et al., New horizons in adjuvants for vaccine development, *Trends Immunol.*, 30(1):23-32 (2009).
Reisser et al., Mechanisms of the antitumoral effect of lipid A, *BioEssays*, 24: 284-9 (2002).
Reiter et al., Prostate stem cell antigen: A cell surface marker overexpressed in prostate cancer, *Proc. Nat. Acad. Sci. USA*, 95(4):1735-40 (1998).
Ribi et al., Beneficial modification of the endotoxin molecule, *J. Biol. Resp. Modifiers*,3:1-9 (1984).
Richards et al., Immunogenicity of liposomal malaria sporozoite antigen in monkeys: Adjuvant effects of aluminum hydroxide and non-pyrogenic liposomal lipid A, *Vaccine*, 7:506-12(1989).
Rietschel et al., Bacterial endotoxin: molecular relationships of structure to activity and function, *FASEB J.*, 8:217-25 (1994).
Rietschel et al., Endotoxic properties of synthetic pentaacyl lipid A precursor Ib and a structural isomer, *Eur. J. Biochem.*, 169:27-31 (1987).

(56) References Cited

OTHER PUBLICATIONS

Rietschel et al., Lipid A, the endotoxic center of bacterial lipopolysaccharides: Relation of chemical structure to biological activity, *Progr. Clin. Biol. Res.*, 231: 25-53 (1987).
Rietschel et al., The chemical structure of bacterial endotoxin in relation to bioactivity, *Immunobiology*, 187:169-90 (1993).
Robbins et al., Human tumor antigens recognized by T-Cells, *Curr. Opin. Immunol.*, 8(5):628-36 (1996).
Rothenberg et al., Stimulation of rabbit synoviocyte prostaglandin E2 synthesis by lipopolysaccharides and their subunit structures, *Arthritis and Rheumatism*, 31(2): 238-47 (1988).
Rubins et al., Pneumolysin in pneumococcal adherence and colonization, *Microb. Pathog.*, 25(6):337-42 (1998).
Rudbach et al., Ribi Adjuvants: Chemistry, biology and utility in vaccines for human and veterinary medicine, theory and practical application of adjuvants, 13:287-313 (1995).
Saiki et al., Inhibition of tumor-induced angiogenesis by the administration of recombinant interferon-gamma followed by a synthetic lipid-A subunit analogue (GLA-60), *Int. J. Cancer*, 51(4): 641-5 (1992)—Abstract only.
Salem et al., The adjuvant effects of the toll-like receptor 3 ligand polyinosinic-cytidylic acid poly (I:C) on antigen-specific CD8+ T cell responses are partially dependent on NK cells with the induction of a beneficial cytokine milieu, *Vaccine*, 24(24):5119-32 (2006).
Salkowski et al., Lipopolysaccharide and monophosphoryl lipid A differentially regulate interleukin-12, Gamma interferon, and interleukin-10 mRNA production in murine macrophages, *Infect. Immunity*, 65(8):3239-47 (1997).
Salomon et al., Cripto: A novel epidermal growth factor (EGF)-related peptide in mammary gland development and Neoplasia, *BioEssays*, 21(1):61-70 (1999).
Schirmbeck et al., Antigenic epitopes fused to cationic peptide bound to oligonucleotides facilitate toll-like receptor 9-Dependent, but CD4+ T cell help-independent priming of CD8+ T cells, *J. Immunol.*, 171(10):5198-207 (2003).
Schmidt et al., Cytokine and Ig-production by CG-containing sequences with phosphorodiester backbone and dumbbell shape, *Allergy*, 61(1):56-63 (2006).
Schnur et al., Leishmanial serotypes as distinguished by the gel diffusion of factors excreted in vitro and in vivo, *Isrl. J. Med. Sci.*, 8(7):932-42 (1972).
Schromm et al., Biological activities of lipopolysaccharides are determined by the shape of their lipid A portion, *Eur. J. Biochem.*, 267:2008-13 (2000).
Second Declaration of Steven Reed, Ph.D. with Appendices A and B, executed on Apr. 30, 2012, filed in U.S. Appl. No. 11/862,122.
Senaldi et al., Serological diagnosis of visceral leishmaniasis by a dot-enzyme immunoassay for the detection of a leishmania donovani-related circulating antigen, *J. Immunol. Methods*, 193(1):9-15 (1996).
Seong et al., Hydrophobicity: an ancient damage-associated molecular pattern that initiates innate immune responses, *Nat. Rev. Immunol.*, 4:469-78 (2004).
Sethi et al., Bacterial infection in Chronic Obstructive Pulmonary Disease in 2000: A State-of-the-Art Review, *Clin. Microbiol. Rev.*, 14(2):336-63 (2001).
Seydel et al., Intrinsic conformation of lipid A is responsible for agonistic and antagonistic activity, *Eur. J. Biochem.*, 267:3032-9 (2000).
Seydel et al., Physicochemical characterization of carboxymethyl lipid A derivatives in relation to biological activity, *FEBS J.*, 272:327-40 (2005).
Seydel et al., Supramolecular structure of lipopolysaccharide and free lipid A under physiological conditions as determined by synchrotron small-angle X-ray diffraction, *Eur. J. Biochem.*, 186:325-32 (1989).
Simon, CRC Desk Reference for Allergy and Asthma, CRC Press LLC, 20-3 (2000).
Soboll et al., Expression of Toll-Like Receptors (TLR) and responsiveness to TLR agonists by polarized mouse uterine epithelial cells in culture, *Biol. Reprod.*, 75(1):131-9 (2006).
Srivastava et al., Costimulatory SA-4-1BBL and monophophoryl lipid A as novel adjuvant system for the development of cancer vaccines with robust therapeutic efficacy, *Cancer Res.*, 1(8): Suppl. 1 (2011)—Abstract 765.
Steers et al., Modulation of immunoproteasome subunits by liposomal lipid A, *Vaccine*, 26:2849-59 (2008).
Stone et al., Nanoparticles-delivered multimeric soluble CD40L DNA combined with toll-like receptor agonists as a treatment for melanoma, *PLoS One*, 4(10): e7334 (2009).
Stover et al., Structure activity relationship of synthetic Toll-Like Receptor 4 agonists, *J. Biol. Chem.*, 279(6):4440-9 (2004).
Szczepanski, et al., Triggering of toll-like receptor 4 expressed on human head and neck squamous cell carcinoma promotes tumor development and protects the tumor from immune attack, *Cancer Res*; 69 (7) 3105-3113 (Apr. 1, 2009).
Takada et al., Immunopharmacological Activities of a Synthetic Counterpart of a Biosynthetic Lipid A precursor molecule and of its analogs, *Infect. Immunity*, 48(1):219-27 (1985).
Takada et al., Structural requirements of lipid A for endotoxicity and other biological activities, *CRC Crit. Rev. Microbiol.*, 16(6):477-523 (1989).
Takada et al., Structural requirements of lipid A species in activation of clotting enzymes from the horseshoe crab, and the human complement cascade, *Eur. J. Biochem.*, 175:573-80 (1988).
Takayama et al., Adjuvant Activity of non-ionic block copolymers V. Modulation of antibody isotype by lipopolysaccharides, lipid A and precursors, *Vaccine*, 9:257-65 (1991).
Takayama et al., Complete structure of lipid a obtained from the lipopolysaccharides of the heptoseless mutant of *Salmonella typhimurium*, *J. Biol. Chem.*, 258(21):12801-3 (1983).
Takayama et al., Influence of fine structure of lipid A in Limulus amebocyte lysate clotting and toxic activities, *Infect. Immun.*, 45(2):350-55 (1984).
Takayama et al., Isolation of a nontoxic lipid A fraction containing tumor regression activity, Cancer Res., 41: 2654-7 (1981).
Takeda et al., Toll-Like Receptors in Innate Immunity, *Int. Immunol.* 17(1):1-14 (2005).
Takeda et al., Toll-like receptors, *Ann. Rev. Immunol.*, 21:335-76 (2003).
Tamai et al., Cell activation by monosaccharide lipid A analogues utilizing Toll-like receptor 4, *Immunology*, 110:66-72 (2003).
Tanamoto, Dissociation of endotoxic activities in a chemically synthesized lipid a precursor after acetylation, *Infect. Immunity*, 63(2):690-2 (1995).
Tanamoto, Salmonella-type heptaacylated Lipid A is inactive and acts as an antagonist of lipopolysaccharide action on human line cells, *J. Immunol.*, 164:3149-56 (2000).
Teghanemt et al., Molecular basis of reduced potency of underacylated endotoxins, *J. Immun.*, 175:4669-76 (2005).
Therisod et al., Helicobacter mustelae lipid A structure differs from that of Helicobacter pylori, *FEBS Lett*,. 499:1-5 (2001).
Thompson et al., The low-toxicity versions of LPS, MPL® adjuvant and RC529, are efficient djuvants for CD4 T cells, *J. Leukoc. Biol.*, 78:1273-80 (2005).
Trent et al., Diversity of endotoxin and its impact on pathogenesis, *J. Endotox. Res.*, 12(4):205-23 (2006).
Triantafilou et al., Combinational clustering of receptors following stimulation by bacterial products determines lipopolysaccharide responses, *Biochem. J.*, 381:527-36 (2004).
Triozzi et al., Effects of a beta-human chorionic gonadotropin subunit immunogen administered in aqueous solution with a novel nonionic block copolymer adjuvant in patients with advanced cancer, *Clin. Cancer Res.*, 3(12 Pt 1):2355-62 (1997).
Tsan et al., Cytokine function of heat shock proteins, *Am. J. Physiol. Cell Physiol.*, 286(4):C739-44 (2004).
Tsan et al., Endogenous ligands of Toll-Like Receptors, *J. Leukoc. Biol.*, 76(3):514-9 (2004).
U.S. Appl. No. 11/862,122, filed Sep. 26, 2007, Final Office Action mailed Feb. 1, 2010.

(56) References Cited

OTHER PUBLICATIONS

U.S. Appl. No. 11/862,122, filed Sep. 26, 2007, Office Action mailed Jul. 28, 2009.
U.S. Appl. No. 11/862,122, filed Sep. 26, 2007, Office Action mailed May 5, 2011.
U.S. Appl. No. 12/351,710, filed Jan. 9, 2009, Office Action mailed Dec. 13, 2010.
Ukei et al., Adjuvant and antitumour activities of synthetic lipid A analogues, *Vaccine*, 4:21-24 (1986).
Ulrich et al., Topics in vaccine adjuvant research, Chapter 12, The Adjuvant Activity of Monophosphoryl Lipid A, 133-43 (1991).
Van De Voort et al., Intratumoral delivery of low doses of anti-CD40 mAb combined with monophosphoryl lipid A induces local and systemic antitumor effects in immunocompetent and T cell-deficient mice, *J. Immunother.*, 36(1): 29-40 (2013).
Van den Eynde et al., Tumor antigens recognized by t-lymphocytes, *Mt. J. Clin. Lab. Res.*, 27:81-6 (1997).
Velasco et al., Toll-Like Receptor 4 or 2 agonists decrease allergic inflammation, *Amer. J. Resp. Cell Molec. Biol.*, 32:218-24 (2005).
Vincent et al., Long-term correction of mouse dystrophic degeneration by adenovirus-mediated transfer of a minidystrophin gene, *Nat. Genet.*, 5(2):130-4 (1993).
Vollmer et al., Immunopharmacology of CpG oligodeoxynucleotides and ribavirin, *Antimicrob. Agents Chemother.*, 48(6):2314-7 (2004).
Vollmer, Progress in drug development of immunostimulatory CpG oligodeoxynucleotide ligands for TLR9, *Exp. Opin. Biolog. Ther.*, 5(5):673-82 (2005).
Vosika et al., Phase-I study of intravenous modified lipid A, *Cancer Immunol. Immunother.*, 18(2): 107-12 (1984)—Abstract only.
Wang et al., Effective antibody therapy induces host-protective antitumor immunity that is augmented by TLR 4 agonist treatment, *Canc. Immunol. Immunother.*, 61(1):49-61 (2011).
Wang et al., Inhibition of endotoxin-induced interleukin-6 production by synthetic lipid A partial structure in human peripheral blood mononuclear cells, *Infect. Immun.*, 59(12):4655-64 (1991).
Wang et al., pH-sensitive Immunoliposomes Mediate Target-Cell-Specific Delivery and Controlled Expression of a Foreign Gene in Mouse, *Proc. Natl. Acad. Sci. USA*, 84:7851-5 (1987).
Wasylyk et al., The Ets Family of Transcription Factors, *Eur. J. Biochem.*, 211(1-2):7-18 (1993).
Webpage from List Biological Laboratories, Inc. showing the 'order products online' page for lipopolysaccharides.
Weeratna et al., TLR Agonists as Vaccine Adjuvants: Comparison of CpG ODN and Resiquimod (R-848), *Vaccine*, 23(45):5263-70 (2005).
Weihrauch et al., Phase I/II Combined chemoimmunotherapy with carcinoembryonic antigen-derived HLA-A2-restricted CAP-1 peptide and irinotecan, 5-Fluorouracil, and leucovorin in patients with primary metastatic colorectal cancer, *Clin. Cancer Res.*, 11(16):5993-6001 (2005).
Wheeler et al., Allergy vaccines—new approaches to an old concept, *Exp. Opin. Biol. Ther.*, 4(9):1473-81 (2004).
Wu et al., Targeting genes: Delivery and persistent expression of a foreign gene driven by mammalian regulatory elements in vivo, *J. Biol. Chem.*, 264(29):16985-87 (1989).
Xiong et al., Inhibition of interleukin-12 p40 Transcription and NF-kB activation by nitric oxide in murine macrophages and dendritic cells, *J. Biol. Chem.*, 279(11):10776-83 (2004).
Yang et al., The immunogenicity-enhancing effect of emulsion vaccine adjuvants is independent of the dispersion type and antigen release rate—a revisit of the role of the hydrophile-lipophile balance (HLB) value, *Vaccine*, 23:2665-75 (2005).
Yasuda et al., Biological activity of chemically synthesized analogues of lipid A, *Euro. J. Biochem.*, 124(2):405-7 (1982).
Yasuda et al., Further study of biological activities of chemically synthesized analogues of lipid A in artificial membrane vesicles, *Eur. J. Biochem.*, 140(2):245-8 (1984).
Yeh et al., Improving protein delivery from microparticles using blends of Poly(DL Lactide Co-Glycolide) and Poly(Ethylene Oxide)-Poly(Propylene Oxide) Copolymers, *Pharm. Res.*, 13(11):1693-8 (1996).
Yoshida et al., Endotoxic properties of chemically synthesized lipid A analogs, *Microbiol. Immunol.*, 33(10):797-810 (1989).
Yoshida et al., Monophosphoryl Lipid A induces pharmacologic 'preconditioning' in rabbit hearts without concomitant expression of 70-kDa heat shock protein, Molec. Cell. Biochem., 156:1-8 (1996).
Yoshikawa et al., Bioactive saponins and glycosides. III. Horse Chestnut. (1): The structures, inhibitory effects on ethanol absorption, and hypoglycemic activity of escins Ia, Ib, IIa, IIb, and IIIa from the seeds of aesculus Hippocastanum L., *Chem. Pharm. Bull.*, 4(8):1454-64 (1996).
Yusuf et al., Protective role of Toll-like Receptor 4 during the Initiation Stage of cutaneous Chemical Carcinogenesis, *Cancer Res.*, 68(2):615-22 (2008).
Zahringer et al., Molecular structure of lipid A, the endotoxic center of bacterial lipopolysaccharides, *Adv. Carbohydrate Chem. Biochem.*, 50:211-76 (1994).
Zijlstra et al., the direct agglutination test for diagnosis of visceral leishmaniasis under field conditions in sudan: comparison of aqueous and freeze-dried antigens, *Trans. R. Soc. Trop. Med. Hyg.*, 91(6):671-3 (1997).

* cited by examiner

No Depletion: n = 25 ; * - from PBS, p<0.01
Depletion: n = 27 ; group differences were not evident

COMPOSITIONS AND METHODS FOR REDUCING OR PREVENTING METASTASIS

CROSS-REFERENCE TO RELATED PATENT APPLICATIONS

This application claims the priority benefit of U.S. provisional application Ser. No. 61/830,675, filed Jun. 4, 2013, which is incorporated herein by reference in its entirety.

FIELD OF THE INVENTION

The present invention relates to the reduction or even prevention of metastasis development using a glucopyranosyl lipid adjuvant (such as GLA or short, SLA), alone or in combination with a COX2 inhibitor and a beta-adrenergic blocker.

BACKGROUND OF THE INVENTION

Despite improvements in early detection of cancer and in therapeutic interventions, overall cancer survival rates have not been markedly improved along the last decades, and metastasis is still the main cause of mortality in most solid malignancies.

It has recently become recognized that the perioperative period of primary tumor resection, namely the time period immediately before, during and following the surgical operation, enfolds several unattended risk factors for long-term cancer recurrence, and is thus characterized by high risk for the outbreak of pre-existing micrometastases and the initiation of new metastases. Most of these perioperative risks are due to various perturbations induced by the surgical removal of the primary tumor, which are believed to facilitate the progression of pre-existing micrometastases and the initiation of new metastases through several mechanisms, some of which have only recently been identified.

Numerous soluble factors are increased systemically during the perioperative period as a result of patients' neuroendocrine and paracrine responses to (i) the presence of the primary tumor, to (ii) physiological and psychological stress, and (iii) to the surgical procedure itself and its accompanying anesthesia, analgesia, blood transfusion and other intra-operative procedures. These soluble compounds include catecholamines, prostaglandins, glucocorticoids, opioids, and a variety of administered anesthetic and analgesic agents. In recent years, it has become clear that in vitro, many of these factors act directly on malignant cells, activating several molecular processes that are critical for tumor metastatic activity, including tumor cell proliferation, adhesion, locomotion, extracellular matrix invasion capacity, resistance to apoptosis and anoikis, and secretion of pro-angiogenic factors. Additionally, in vitro and human and animal in vivo studies show that many of these soluble factors lead to suppression of anti-metastatic cell mediated immunity (CMI), which is indeed a common perioperative phenomenon.

CMI, particularly cytotoxic T lymphocytes (CTL) and natural killer (NK) cells, is suppressed even before surgery, and significantly more so following it, with the degree of suppression corresponding to the extent of surgical trauma and tissue damage. Notably, the suppression of CMI had been causally shown to mediate promotion of cancer metastasis in animal models, and clinical studies had associated it with increased susceptibility to metastatic development.

Among the various treatments aiming at reducing malignant tissue and/or preventing suppression of CMI, immunotherapy in cancer patients has regained momentum in the past decade. Specifically, type 1 T-helper (Th1) and proinflammatory cytokines (e.g. IL-2, IL-12, IFN-γ) are known to significantly enhance CMI, which plays a crucial role in the in vivo eradication of malignant cells. Immune-stimulatory approaches (ISAs) commonly utilize established biological response modifiers (BRMs), which include natural or synthetic compounds containing pathogen-associated molecular patterns (e.g. LPS, CpG), or the pro-inflammatory/Th1 cytokines that these compounds induce.

However, while animal studies employing anti-tumor ISAs showed promising results, clinical studies in cancer patients were, by-and-large, less successful. Several difficulties in simulating the development of human cancer in animal models were suggested to underlie this discrepancy, most focusing on differences in the biology of the implanted cancerous tissue and host physiology, including immune susceptibility and compatibility to implanted tissue. Stress responses, known to induce an immunossupressing effect, which result from psychological and physiological conditions that characterize cancer patients and absent in animal models, were also suggested to underlie this discrepancy.

Neeman et al. (2012) *Clin Cancer Res.*, 18(18): 4895-902 describe an approach to reducing postsurgical cancer recurrence, by perioperative targeting of catecholamines and prostaglandins using simultaneous beta-adrenergic blockade and COX-2 inhibition.

Avraham et al. (2010) *Brain Behav Immun.*, 24(6):952-8 describe an integration of immunostimulatory therapy with endocrine-blocker pharmacological interventions that prevent postoperative immunosuppression, to reduce post-operative tumor progression.

Despite the acknowledged importance of the perioperative period, and the promising results evident in animal studies employing ISAs, immune-stimulatory therapy has rarely been utilized in patients during the perioperative period, presumably due to the expected pyrogenic and adverse effects of ISAs that cannot be distinguished from signs of life-threatening infections in the context of surgery. The relatively few clinical trials that had attempted this approach utilized a single Th1 (e.g., IL-2, IL-12) or a proinflammatory (e.g., IFN-α) cytokine, and have indeed reported severe adverse reactions to these therapies, including leukopenia, deterioration of performance status, fever, vomiting, and mental depression. Recently FDA-approved synthetic agents, which are based on pathogen-associated molecular patterns (PAMPs), have been shown to cause markedly less adverse reactions while inducing an effective, self-controlled, endogenous, multi-cytokine response. Such ISAs include the TLR-4 agonists, termed glucopyranosyl lipid adjuvants (GLAs as disclosed in U.S. Pat. No. 8,273, 361 and WO 2010/141861), which activate T, B, and Dendritic cells.

U.S. Pat. No. 8,273,361 discloses compositions and methods, including vaccines and pharmaceutical compositions for inducing or enhancing an immune response, based on the discovery of useful immunological adjuvant properties of a synthetic, glucopyranosyl lipid adjuvant (GLA) that is provided in a substantially homogeneous chemical form. Also provided are vaccines and pharmaceutical compositions that include GLA and one or more antigens, a Toll-like receptor (TLR) agonist, a co-adjuvant and a carrier such as a pharmaceutical carrier.

WO 2010/141861 discloses compounds, particularly, glucopyranosyl lipid adjuvant (GLA) compounds with an alternate chemical structures and properties. Pharmaceutical compositions, vaccine compositions, and related methods for inducing or enhancing immune responses, are also disclosed.

There still remains a need for more effective treatments against the development of metastases.

All publications, patents, and patent applications cited herein are hereby incorporated by reference in their entirety for all purposes.

SUMMARY OF THE INVENTION

The present invention provides compositions and methods for reducing or preventing the formation of cancer metastasis using glucopyranosyl lipid adjuvants (GLA). According to some embodiments, the present invention is directed to the reduction or prevention of metastasis development using local-regional delivery of GLA. According to some embodiments, GLA is used without co-administration of a cancer antigen (whether as a defined peptide, protein, or mixture of peptides, proteins or fragments, or as an inactivated or modified cancer cell preparation). According to some embodiments, GLA is combined with a COX2 inhibitor and a beta-adrenergic blocker.

The present invention discloses for the first time local-regional delivery of GLA to a space or cavity adjacent to a tumor to be treated, or alternatively to a space or cavity adjacent to, or directly into, a draining lymph node of a tumor to be treated. Such local-regional delivery of GLA can also be performed after removal of a primary tumor, to a space or void formed after the resection of a tumor mass. The present invention thus provides a more controlled manner of administration of GLA, to improve treatment outcome. Advantageously, local-regional delivery can provide a more sustained effect of the active ingredient. Additionally, local-regional delivery of GLA can allow for lower total body dosing of GLA and the reduction of deleterious side effects that can be associated with systemic delivery in a cancer setting.

The present invention further discloses the use of GLA against cancer metastasis without co-administration of a cancer antigen, such as an antigen derived from the tumor of the subject being treated, an antigen or antigen composition containing antigens known to be associated with the tumor type of the subject being treated, or a preparation of antigens derived from administration of tumor cells or preparation of tumor cells from the patient or a mixture of patient defined tumors, thus differing from administration of GLA in the context of a composition for a cancer vaccine. Advantageously, in the present invention such use of GLA is not limited to types of cancer for which cancer-specific antigens have been identified.

In some embodiments, GLA is utilized for the prevention of metastasis of a solid tumor, following a tumor excision surgery. It is now disclosed that GLA administered prior to and following surgery, achieves effective inhibition of metastatic development.

The present invention further discloses that GLA treatment can be combined with treatment with a beta-adrenergic blocker and/or a COX2-selective inhibitor, to further optimize the outcome of metastasis inhibition. Without being bound by any particular theory or mechanism of action, it is contemplated that the combination of a beta-adrenergic blocker and a COX2 inhibitor counteracts stress-induced immunosuppression which may occur in cancer patients, thus resulting in improved efficacy of GLA. The combination of active ingredients disclosed herein act at least additively and preferably synergistically.

In one aspect, the invention provides a method of treating a subject having cancer, the method comprising the step of administering to the subject a pharmaceutical composition comprising a glucopyranosyl lipid adjuvant (GLA) or a pharmaceutically acceptable salt thereof as an active ingredient, wherein said administration is effective in treating cancer.

According to one aspect, the present invention provides a method for reducing or preventing metastasis development in a subject, the method comprising the step of administering to the subject a pharmaceutical composition comprising a glucopyranosyl lipid adjuvant (GLA) or a pharmaceutically acceptable salt thereof as an active ingredient, wherein said administration is effective in reducing or preventing metastasis.

As used herein, the terms "metastasis", "cancer metastasis" or "tumor metastasis" are used interchangeably and refer to the growth of cancerous cells derived from a primary cancerous tumor located in one organ or tissue, in another, non-adjacent organ or tissue. Metastasis also encompasses micrometastasis, which is the presence of an undetectable amount of cancerous cells in an organ or body part which is not directly connected to the organ of the original, primary cancerous tumor. Metastasis can also be defined as several steps of a process, such as the departure of cancer cells from an original tumor site, and migration and/or invasion of cancer cells to other parts of the body.

As used herein, "reduction or prevention of metastasis development" refers to slowing or even completely inhibiting the spread, development and growth of metastasis. The term may also include reducing the number of metastases in an organ or tissue, as well as reducing the size, number or malignancy status of an existing cancer to be treated by the compositions of the invention. As one of ordinary skill in the art would understand a reduction or prevention of metastasis development can be measured by standard methodologies known in the art including a reduction in size or numbers of tumors as measured by a variety of radiographic, imaging, circulating tumor marker, palpitation, direct measurement or observation techniques known in the art. Accordingly a reduction or prevention of metastasis development can also be measured by a reduction of a sign or symptom associated with the disease state of the cancer being treated or a prolongation of survival or reduction in suffering from a disease sign or symptom of the cancer being treated.

In some embodiments, GLA or a pharmaceutically acceptable salt thereof is administered by local-regional delivery.

As used herein "local-regional delivery" indicates delivery to a space or cavity adjacent to a tumor to be treated, or delivery to a space or cavity adjacent to, or directly into, a draining lymph node of a tumor to be treated. If administered after tumor excision surgery, local-regional delivery includes delivery to the space or void formed after the removal of the tumor mass. Local-regional administration can be performed by a single injection to a single or multiple local-regional space, or as a series of injections given concurrently or over a period of at least about a minute, minutes, hours, days or weeks. As used herein, local-regional delivery does not include intra-tumor administration. Additionally, local-regional administration does not include topical administration, where a pharmaceutical composition is applied onto an external body surface of a subject.

In some embodiments, GLA or a pharmaceutically acceptable salt thereof is administered without a cancer-antigen.

In some embodiments, the administered pharmaceutical composition comprising GLA or a pharmaceutically acceptable salt thereof is substantially devoid of a cancer-antigen.

"Substantially devoid" as used herein refers to less than about 1%, preferably less than about 0.1%, less than about 0.01% (w/w), less than about 0.001% (w/w).

In some embodiments, the method is used for reducing or preventing metastasis development in a subject following a tumor excision surgery. In some embodiments, GLA or a pharmaceutically acceptable salt thereof is administered during the perioperative period of said tumor excision surgery.

The "perioperative period" refers to the time period immediately before, during and immediately after surgery. It includes the time preceding an operation, when a patient is being prepared for surgery ("the preoperative period"), followed by the time spent in surgery ("the intraoperative period") and by the time following an operation when the patient is recovering and usually being monitored for complications ("the postoperative period"). The perioperative period can occur in hospitals, surgical centers and/or health care providers' offices.

As used herein, the perioperative period typically refers to a period beginning 2-10 days prior to a tumor excision surgery and ending 14-21 days following said surgery, for example beginning 4-5 days prior to surgery and ending about 14 days following surgery, or beginning 7 days prior to surgery and ending about 7 days following surgery.

In some embodiments, GLA or a pharmaceutically acceptable salt thereof is administered at least one time (for example two time, three times, four times or more) before the surgery. In some embodiments, GLA or a pharmaceutically acceptable salt thereof is administered at least one time (for example two time, three times, four times or more) after the surgery. In some embodiments, GLA or a pharmaceutically acceptable salt thereof is administered both before and after surgery.

In some embodiments, where GLA or a pharmaceutically acceptable salt thereof is administered a plurality of times, it is administered in constant doses. According to these embodiments, each time GLA or a pharmaceutically acceptable salt thereof is administered, it is administered in the same dose. In other embodiments, where GLA or a pharmaceutically acceptable salt thereof is administered a plurality of times, it is administered in varying doses. According to these embodiments, the administered dose of GLA or a pharmaceutically acceptable salt thereof varies throughout the treatment period.

In some embodiments, GLA has the following structural formula (I):

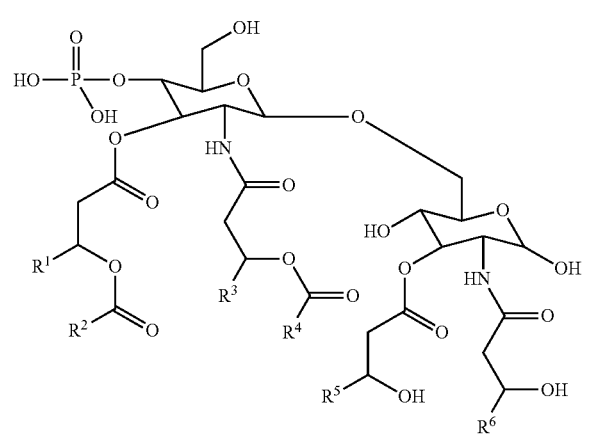

(I)

wherein: $R^1$, $R^3$, $R^5$ and $R^6$ are $C_{11}$-$C_{20}$ alkyl; and $R^2$ and $R^4$ are $C_{12}$-$C_{20}$ alkyl.

In some embodiments, $R^1$, $R^3$, $R^5$ and $R^6$ are undecyl and $R^2$ and $R^4$ are tridecyl.

In some embodiments, GLA has the following structural formula (II):

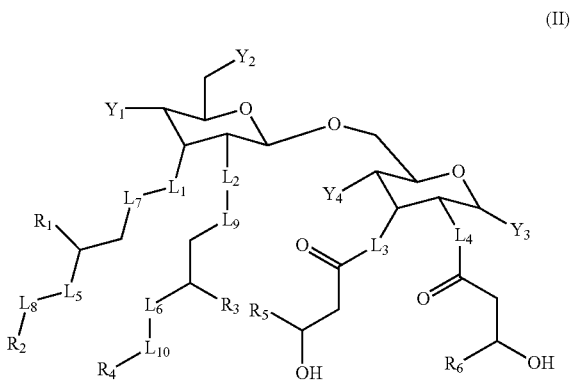

(II)

wherein:
$L_1$, $L_2$, $L_3$, $L_4$, $L_5$ and $L_6$ are the same or different and independently —O—, —NH— or —(CH$_2$)—;
$L_7$, $L_8$, $L_9$, and $L_{10}$ are the same or different and independently absent or —C(=O)—;
$Y_1$ is an acid functional group;
$Y_2$ and $Y_3$ are the same or different and independently —OH, —SH, or an acid functional group;
$Y_4$ is —OH or —SH;
$R_1$, $R_3$, $R_5$ and $R_6$ are the same or different and independently $C_8$-$C_{13}$ alkyl; and
$R_2$ and $R_4$ are the same or different and independently $C_6$-$C_{11}$ alkyl.

In certain embodiments, a GLA adjuvant used herein may have the following structural formula (III):

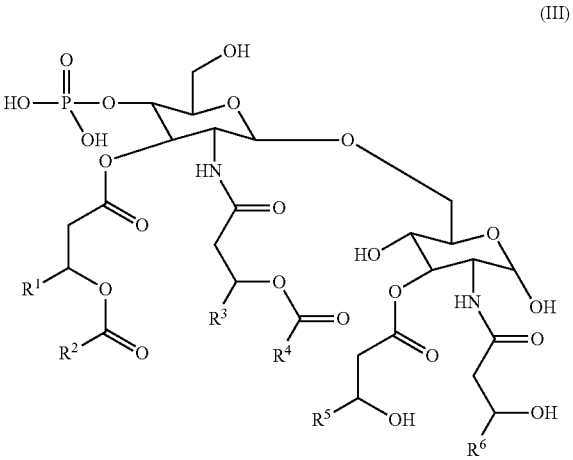

(III)

wherein:
$R^1$, $R^3$, $R^5$ and $R^6$ are $C_{11}$-$C_{20}$ alkyl; and $R^2$ and $R^4$ are $C_9$-$C_{20}$ alkyl.

In a more specific embodiment, the GLA has formula III set forth above wherein $R^1$, $R^3$, $R^5$ and $R^6$ are $C_{11-14}$ alkyl; and $R^2$ and $R^4$ are $C_{12-15}$ alkyl.

In a more specific embodiment, the GLA has formula III set forth above wherein $R^1$, $R^3$, $R^5$ and $R^6$ are $C_{11}$ alkyl; and $R^2$ and $R^4$ are $C_{13}$ alkyl.

In a more specific embodiment, the GLA has formula III set forth above wherein $R^1$, $R^3$, $R^5$ and $R^6$ are $C_{11}$ alkyl; and $R^2$ and $R^4$ are $C_9$ alkyl.

In certain embodiments, the GLA is synthetic and has the following structural formula (IV):

(IV)
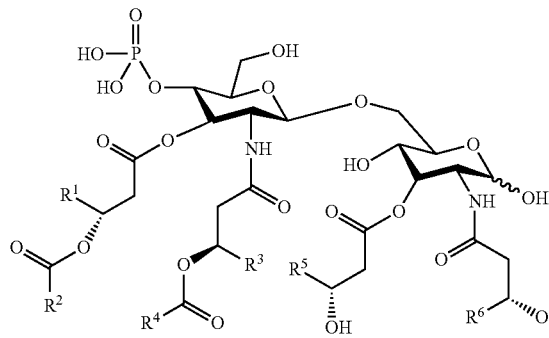

In certain embodiments of the above GLA structure (formula IV), $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the GLA is synthetic and has the following structural formula (V):

(V)
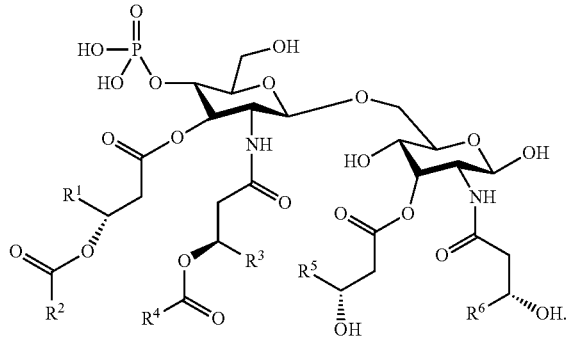

In certain embodiments of the above GLA structure (formula V), $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the GLA is synthetic and has the following structural formula (VI):

(VI)
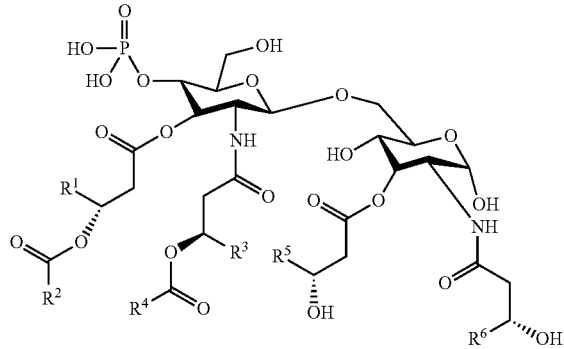

In certain embodiments of the above GLA structure (formula VI), $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the synthetic GLA has the following structure:

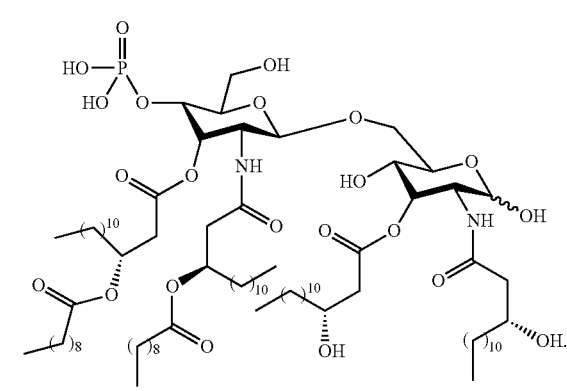

In certain embodiments, the synthetic GLA has the following structure:

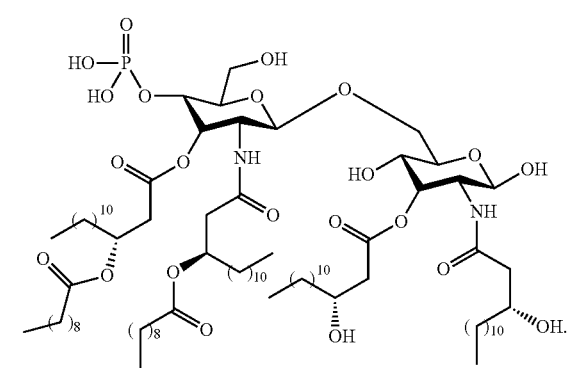

In certain embodiments, the synthetic GLA has the following structure:

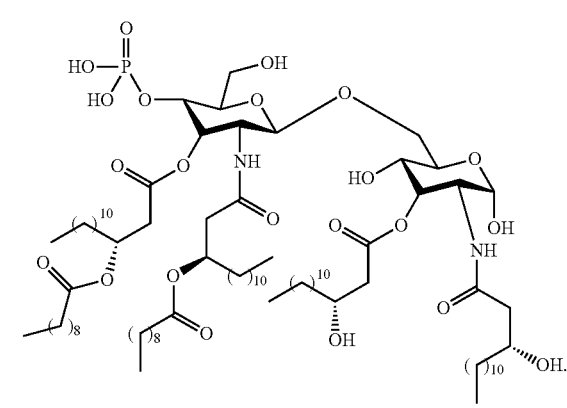

In some embodiments, the method of the present invention further comprises the step of administering a beta-adrenergic blocker and a COX2 inhibitor.

In some embodiments, administration of the beta-adrenergic blocker and COX2 inhibitor is carried out during the perioperative period of a tumor excision surgery.

In some typical embodiments, the beta-adrenergic blocker and COX2 inhibitor are present within separate pharmaceutical compositions.

In some embodiments, the beta-adrenergic blocker, COX2 inhibitor or both are administered at least one time (for example two time, three times, four times or more) before the surgery. In additional embodiments, the beta-adrenergic blocker, COX2 inhibitor or both are administered at least one time (for example two time, three times, four times or more) after the surgery. In some embodiments, the beta-adrenergic blocker, COX2 inhibitor or both are administered both before and after surgery.

In some embodiments, GLA or a pharmaceutically acceptable salt thereof, beta-adrenergic blocker and COX2 inhibitor are administered on the same days during the perioperative period. In other embodiments they are administered on separate days.

In some embodiments, the beta-adrenergic blocker is selected from the group consisting of acebutolol, atenolol, betaxolol, bisoprolol, carteolol, carvedilol, celiprolol, esmolol, labetalol, metoprolol, nadolol, nebivolol, oxyprenolol, penbutolol, pindolol, propranolol, sotalol, timolol, or pharmaceutically acceptable salts thereof. Each possibility represents a separate embodiment of the present invention. In particular embodiments, it is propranolol or a pharmaceutically acceptable salt thereof.

In some embodiments, the COX2 inhibitor is selected from the group consisting of celecoxib, cimicoxib, etoricoxib, etodolac, eoricoxib, lumiracoxib, meloxicam, parecoxib, rofecoxib, tiracoxib, valdecoxib, or pharmaceutically acceptable salts thereof. Each possibility represents a separate embodiment of the present invention. In particular embodiments, it is etodolac or a pharmaceutically acceptable salt thereof.

According to another aspect, the present invention provides a pharmaceutical composition comprising GLA or a pharmaceutically acceptable salt thereof as an active ingredient, for use in the reduction or prevention of metastasis development, said composition being substantially devoid of a cancer antigen.

In some embodiments, the pharmaceutical composition consists of GLA or a pharmaceutically acceptable salt thereof as the sole active ingredient.

In some embodiments, the pharmaceutical composition is formulated for local-regional delivery.

In some embodiments, the pharmaceutical composition is for use during the perioperative period of a tumor excision surgery.

In some embodiments, the pharmaceutical composition is for use with a beta-adrenergic blocker and a COX2 inhibitor during the perioperative period of a tumor excision surgery.

These and further aspects and features of the present invention will become apparent from the figures, detailed description, examples and claims which follow.

DETAILED DESCRIPTION OF THE INVENTION

Figure 1A:
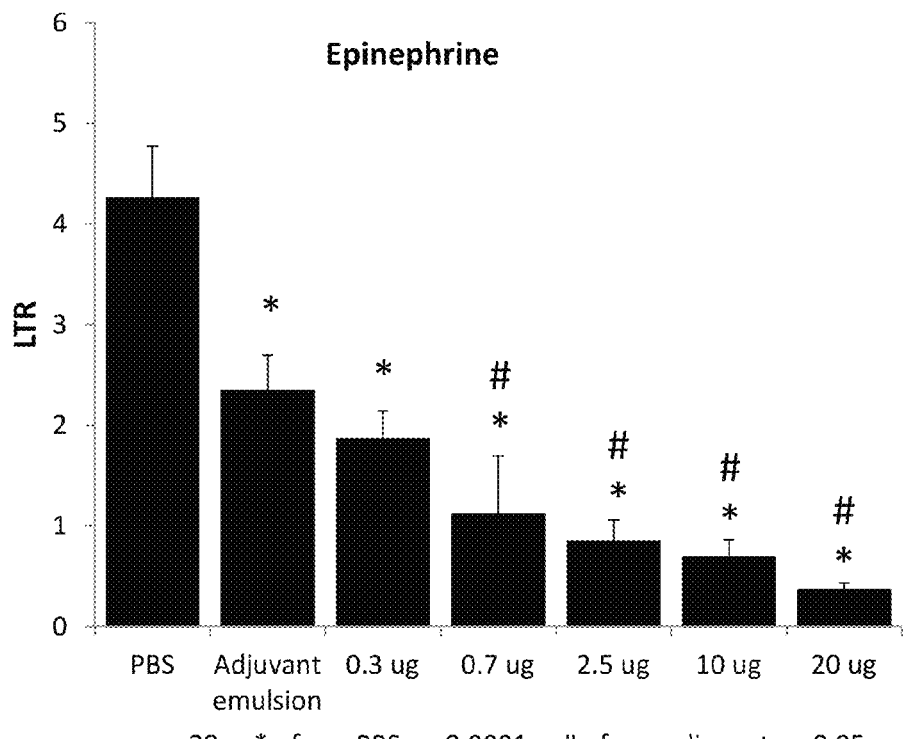
FIG. 1A and FIG. 1B: Dose curve of the effects of GLA on MADB 106 LTR in male rats with (FIG. 1A) or without (FIG. 1B) epinephrine.

The present invention is directed to the reduction or even prevention of metastasis formation. The approach disclosed herein is based on immune-stimulation with GLA. GLA may optionally be combined with a COX2 inhibitor and a beta-adrenergic blocker.

Pharmaceutical Compositions

In one aspect, the pharmaceutical compositions of the present invention may comprise at least one GLA compound, in combination with pharmaceutically acceptable carriers, excipients or diluents. In another aspect, the pharmaceutical compositions of the present invention generally comprise at least one GLA compound, a beta-adrenergic blocker such as propranolol, or a COX2-selective inhibitor such as etodolac, in combination with pharmaceutically acceptable carriers, excipients or diluents. Pharmaceutically acceptable salts of the active agents described herein are also within the scope of the present invention. "Pharmaceutically acceptable salt" refers to salts of the compounds described herein derived from the combination of such compounds and an organic or inorganic acid (acid addition salts) or an organic or inorganic base (base addition salts). The compositions of the present invention may be used in either the free base or salt forms, with both forms being considered as being within the scope of the present invention.

Glucopyranosyl Lipid Adjuvant (GLA):

GLA is a synthetic TLR-4 agonist, capable of eliciting an immune response in a host, particularly cell-mediated immune response. GLA differs from other TLR-4 agonists, such as LPS, MPL and 3-DMPL, by being totally synthetic and having a defined number, length, and position of carbon chains. GLA is capable of eliciting an efficient Th1 activation, while causing only minimal adverse Th2 effects. Compositions comprising GLA are described, for example, in U.S. Pat. No. 8,273,361 and WO 2010/141861.

A GLA molecule for use with the compositions of the present invention comprises: (i) a diglucosamine backbone having a reducing terminus glucosamine linked to a non-reducing terminus glucosamine through an ether linkage between hexosamine position 1 of the non-reducing terminus glucosamine and hexosamine position 6 of the reducing terminus glucosamine; (ii) an O-phosphoryl group attached to hexosamine position 4 of the non-reducing terminus glucosamine; and (iii) up to six fatty acyl chains; wherein one of the fatty acyl chains is attached to 3-hydroxy of the reducing terminus glucosamine through an ester linkage, wherein one of the fatty acyl chains is attached to a 2-amino of the non-reducing terminus glucosamine through an amide linkage and comprises a tetradecanoyl chain linked to an alkanoyl chain of greater than 12 carbon atoms through an ester linkage, and wherein one of the fatty acyl chains is attached to 3-hydroxy of the non-reducing terminus glucosamine through an ester linkage and comprises a tetradecanoyl chain linked to an alkanoyl chain of greater than 12 carbon atoms through an ester linkage. GLA is typically not 3'-de-O-acylated.

A GLA as used herein may have the following structural formula (I):

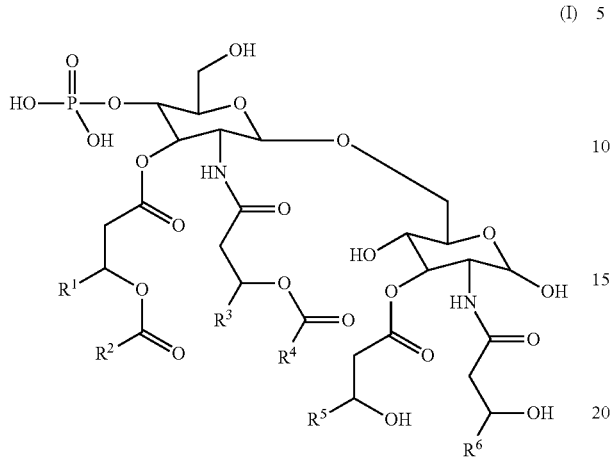

wherein:

$R^1$, $R^3$, $R^5$ and $R^6$ are $C_{11}$-$C_{20}$ alkyl; and $R^2$ and $R^4$ are $C_{12}$-$C_{20}$ alkyl.

A particular example is a GLA wherein $R^1$, $R^3$, $R^5$ and $R^6$ are undecyl and $R^2$ and $R^4$ are tridecyl).

In addition, a GLA as used herein may have the following structural formula (II):

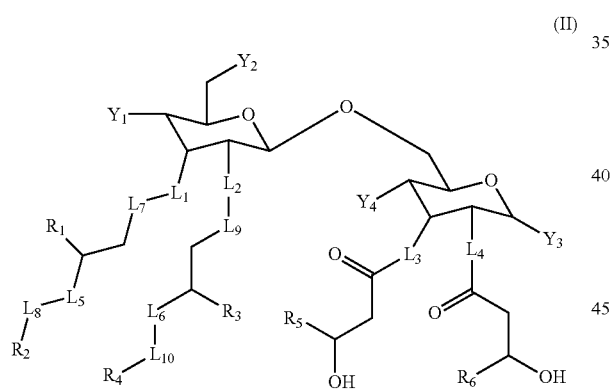

wherein:

$L_1$, $L_2$, $L_3$, $L_4$, $L_5$ and $L_6$ are the same or different and independently —O—, —NH— or —(CH$_2$)—;

$L_7$, $L_8$, $L_9$, and $L_{10}$ are the same or different and independently absent or —C(=O)—;

$Y_1$ is an acid functional group;

$Y_2$ and $Y_3$ are the same or different and independently —OH, —SH, or an acid functional group;

$Y_4$ is —OH or —SH;

$R_1$, $R_3$, $R_5$ and $R_6$ are the same or different and independently $C_8$-$C_{13}$ alkyl; and $R_2$ and $R_4$ are the same or different and independently $C_6$-$C_{11}$ alkyl.

Examples of suitable GLA molecules that can be used are described in WO 2010/141861 noted above.

In certain embodiments, a GLA adjuvant used herein may have the following structural formula (III):

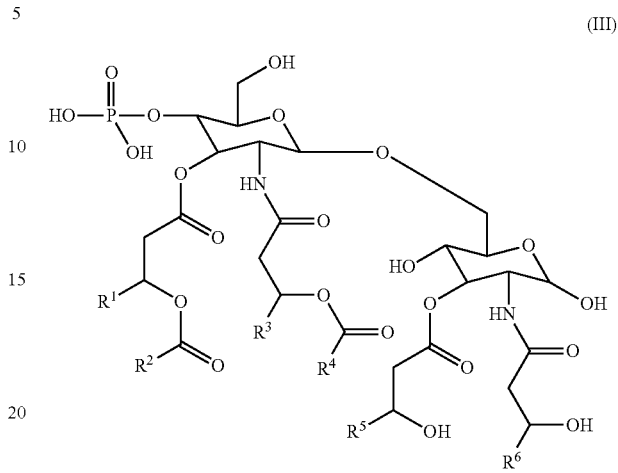

wherein:

$R^1$, $R^3$, $R^5$ and $R^6$ are $C_{11}$-$C_{20}$ alkyl; and $R^2$ and $R^4$ are $C_9$-$C_{20}$ alkyl.

In a more specific embodiment, the GLA has formula III set forth above wherein $R^1$, $R^3$, $R^5$ and $R^6$ are $C_{11-14}$ alkyl; and $R^2$ and $R^4$ are $C_{12-15}$ alkyl.

In a more specific embodiment, the GLA has formula III set forth above wherein $R^1$, $R^3$, $R^5$ and $R^6$ are $C_{11}$ alkyl; and $R^2$ and $R^4$ are $C_{13}$ alkyl.

In a more specific embodiment, the GLA has formula III set forth above wherein $R^1$, $R^3$, $R^5$ and $R^6$ are $C_{11}$ alkyl; and $R^2$ and $R^4$ are $C_9$ alkyl.

In certain embodiments, the GLA is synthetic and has the following structural formula (IV):

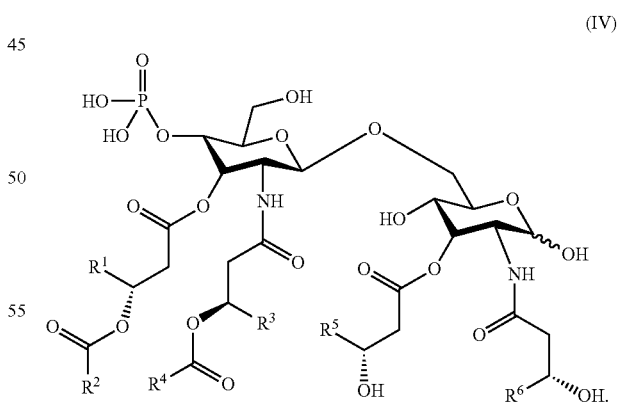

In certain embodiments of the above GLA structure (formula IV), $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the GLA is synthetic and has the following structural formula (V):

(V)

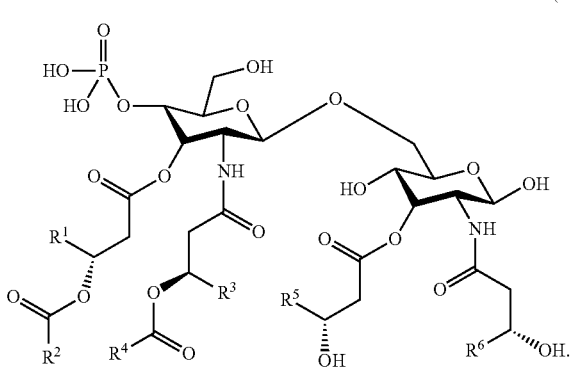

In certain embodiments of the above GLA structure (formula V), $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the GLA is synthetic and has the following structural formula (VI):

(VI)

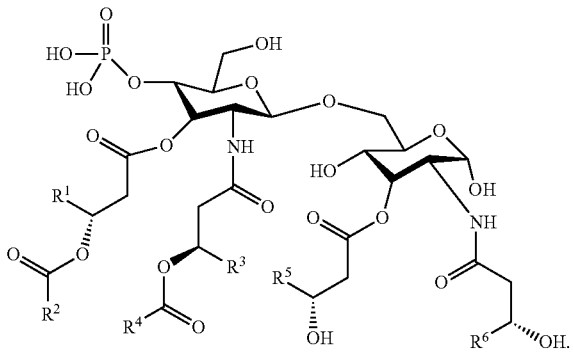

In certain embodiments of the above GLA structure (formula VI), $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the synthetic GLA has the following structure:

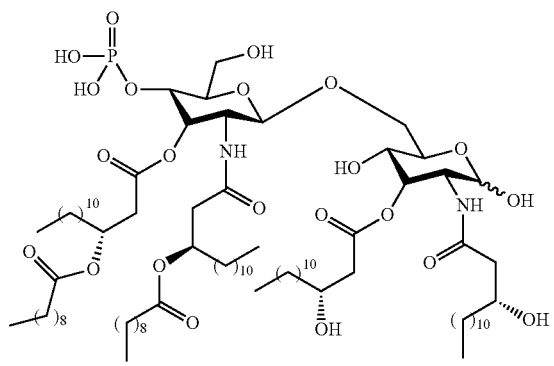

In certain embodiments, the synthetic GLA has the following structure:

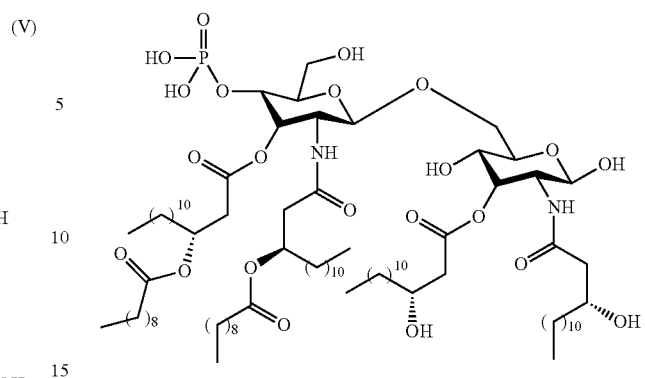

In certain embodiments, the synthetic GLA has the following structure:

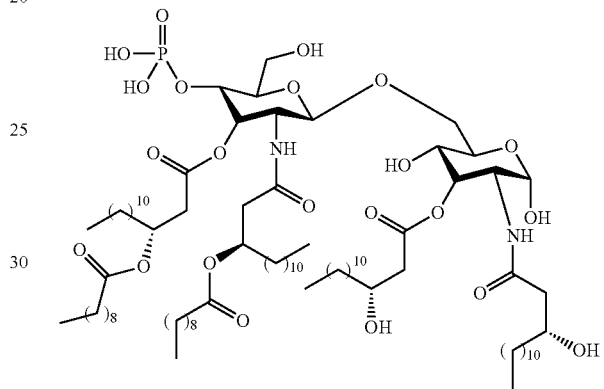

"Alkyl" means a straight chain or branched, noncyclic or cyclic, unsaturated or saturated aliphatic hydrocarbon containing from 1 to 20 carbon atoms, and in certain preferred embodiments containing from 11 to 20 carbon atoms. Representative saturated straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Acid functional group" means a functional group capable of donating a proton in aqueous media (i.e. a Brønsted-Lowry acid). After donating a proton, the acid functional group becomes a negatively charged species (i.e. the conjugate base of the acid functional group). Examples of acid functional groups include, but are not limited to: —OP(=O)(OH)$_2$ (phosphate), —OS(=O)(OH)$_2$ (sulfate), —OS(OH)$_2$ (sulfite), —C(═O)OH (carboxylate), —OC(═O)CH(NH$_2$)CH2C(═O)OH (aspartate), —OC(═O)CH$_2$CH$_2$C(═O)OH (succinate), and —OC(═O)CH$_2$OP(═O)(OH)$_2$ (carboxymethylphosphate).

GLA be obtained commercially. Methods for the synthesis of GLA are provided, for example, in WO 2010/141861 noted above.

GLA formulations can be prepared in substantially homogeneous form, which refers to a GLA preparation that is at least 80%, preferably at least 85%, more preferably at least 90%, more preferably at least 95% and still more preferably at least 96%, 97%, 98% or 99% pure with respect to the GLA molecule. Determination of the degree of purity of a given GLA preparation can be readily made by those familiar with the appropriate analytical chemistry methodologies, such as by gas chromatography, liquid chromatography, mass spectroscopy and/or nuclear magnetic resonance analysis.

The pharmaceutical compositions comprising GLA of the present invention are preferably substantially devoid of cancer-specific antigen(s), and are administered to a subject in order to stimulate an immune response, e.g., a non-specific immune response.

"Substantially devoid" as used herein refers to less than about 1%, preferably less than about 0.1%, less than about 0.01% (w/w), less than about 0.001% (w/w).

The term "about", when referring to a measurable value such as an amount, is used herein to encompass variations of +/−10%, more preferably +/−5%, even more preferably +/−1%, and still more preferably +1-0.1% from the specified value, as such variations are appropriate to achieve the intended purpose.

The GLA may be preferably formulated in a stable emulsion. In one particular embodiment, for example, a composition is provided comprising GLA in a stable emulsion substantially devoid of cancer antigens. Emulsion systems include single or multiphase emulsion systems, as known in the art.

In some embodiments, the composition is in the form of an oil-in-water emulsion. In other embodiments, the composition is in the form of a water-in-oil emulsion. In yet other embodiments, the composition is in the form of microparticles.

In a particular embodiment, a composition of the invention comprises an emulsion of oil in water wherein the GLA is incorporated in the oil phase.

In order for any oil in water composition to be suitable for human administration, the oil phase of the emulsion system preferably comprises a metabolizable oil. The meaning of the term metabolizable oil is well known in the art. Metabolizable can be defined as "being capable of being transformed by metabolism". The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils are also part of this invention and can include commercially available oils such as NEOBEE® and others. A non-limiting example of a suitable oil is Squalene (2,6,10,15,19,23-Hexamethyl-2,6,10,14,18,22-tetracosahexaene).

Oil emulsion preparations of the present invention may comprise an antioxidant, for example the oil α-tocopherol (vitamin E, EP 0 382 271 B1).

WO 95/17210 and WO 99/11241 disclose emulsion adjuvant compositions based on squalene, α-tocopherol, and TWEEN® 80. WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion are preferably less than about 1 micron, may be in the range of about 30-600 nm, preferably about around 30-500 nm in diameter, and most preferably about 150-500 nm in diameter, and in particular about 150 nm in diameter as measured by photon correlation spectroscopy. In this regard, about 80% of the oil droplets by number should preferably be within the preferred ranges, more preferably more than about 90% and most preferably more than about 95% of the oil droplets by number are within the defined size ranges. The amounts of the components present in the oil emulsions of the present invention are conventionally in the range of from about 2 to 10% oil, such as squalene; and when present, from about 2 to 10% alpha tocopherol; and from about 0.3 to 3% surfactant, such as polyoxyethylene sorbitan monooleate. Preferably the ratio of oil:alpha tocopherol is equal or less than 1 as this provides a more stable emulsion. Span 85 may also be present at a level of about 1%. In some cases it may be advantageous that the GLA compositions of the present invention will further contain a stabilizer.

The method of producing oil in water emulsions is well known to the person skilled in the art. Commonly, the method comprises mixing the oil phase with a surfactant such as a PBS/TWEEN80® solution, followed by homogenization using a homogenizer. For instance, a method that comprises passing the mixture once, twice or more times through a syringe needle would be suitable for homogenizing small volumes of liquid. Equally, the emulsification process in a microfluidiser (M110S microfluidics machine, maximum of 50 passes, for a period of 2 minutes at maximum pressure input of 6 bar (output pressure of about 850 bar)) could be adapted to produce smaller or larger volumes of emulsion. This adaptation could be achieved by routine experimentation comprising the measurement of the resultant emulsion until a preparation was achieved with oil droplets of the required diameter.

Exemplary doses of GLA can range from about 0.01 μg/kg to about 100 mg/kg body weight, such as from about 1 μg/kg to about 1 mg/kg, or about 1 μg/kg to about to about 60 μg/kg, or about 5 μg/kg to about 200 μg/kg.

In some embodiments, the pharmaceutical compositions comprising GLA of the present invention are formulated for local-regional delivery. Examples of suitable routes of administration include intradermal, subcutaneous, intramuscular, intraperitoneal. It will be evident to those skilled in the art that the number and frequency of administration will be dependent upon the response of the host.

Beta-Adrenergic Blocker (Antagonist)—e.g., Propranolol:

Propranolol may be identified by CAS Registry Number 525-66-6. It is commercially available and may also be synthesized by methods known in the art. For pharmaceutical compositions, propranolol hydrochloride is typically used. Suitable formulations include, for example, oral solid dosage forms containing about 10-80 mg, oral liquid dosage forms containing about 20-40 mg/5 ml, extended release oral dosage forms containing about 60-160 mg, and intravenously injectable liquid dosage forms containing about 1 mg/ml of propranolol hydrochloride.

COX2-Selective Inhibitor—e.g., Etodolac:

Etodolac may be identified by CAS Registry Number 41340-25-4. It is commercially available and may also be synthesized by methods known in the art. Suitable formulations include, for example, oral solid dosage forms containing about 200-500 mg, extended release oral dosage forms containing about 400-600 mg.

The amount of compounds in the compositions of the present invention which will be effective in the treatment of a particular condition will depend on the nature of the condition, and can be determined by standard clinical techniques. See, for example, Goodman and Gilman; The Physician's Desk Reference, Medical Economics Company, Inc., Oradell, N.J., 1995; and to Drug Facts and Comparisons, Facts and Comparisons, Inc., St. Louis, Mo., 1993.

The precise dose to be employed in the formulation will also depend on the route of administration, and the seriousness of the disease, and should be decided according to the judgment of the practitioner and each patient's circumstances.

Methods and Uses

According to an aspect of the present invention, the present invention provides a method for reducing or preventing metastasis development in a subject.

In some embodiments, the method comprises the step of administering a pharmaceutical composition comprising glucopyranosyl lipid adjuvant (GLA) or a pharmaceutically acceptable salt thereof as an active ingredient.

In some embodiments, a method is provided for reducing or preventing metastasis development in a subject by administering to the subject GLA alone or in combination with a beta-adrenergic blocker and a COX2 inhibitor loco-regionally. In some embodiments, a method is provided for reducing or preventing metastasis development in a subject by administering to the subject GLA alone or in combination with a beta-adrenergic blocker and a COX2 inhibitor loco-regionally without tumor excision.

In some embodiments, a method is provided for reducing or preventing metastasis development in a subject following a tumor excision surgery by administering to the subject GLA alone or in combination with a beta-adrenergic blocker and a COX2 inhibitor during the perioperative period of the tumor excision surgery, thereby reducing or preventing metastasis development following the surgery.

In some embodiments, GLA is administered before (pre-operative) and after (post-operative) surgery. In some embodiments, the beta-adrenergic blocker, COX2 inhibitor or both are administered before (pre-operative) and after (post-operative) surgery.

Administration of GLA is typically performed by local-regional delivery. Under certain circumstances, for example during the perioperative period, systemic administration is used. Systemic administration as used herein does not include intravenous administration.

GLA administration can be performed as a single injection or multiple injections.

Typically, the method of the present invention comprises administering GLA without a cancer antigen. The administered pharmaceutical composition of GLA is preferably substantially devoid of a cancer antigen.

In some embodiments, the method of the present invention further comprises co-administration of a beta-adrenergic blocker and a COX2 inhibitor during the perioperative period.

In some embodiments, GLA is administered pre-operatively, while the beta-adrenergic blocker and/or COX2 inhibitor are administered pre- and post-operatively.

In some embodiment, all three active ingredients are administered both before and after surgery.

The particular doses of each of the active ingredients, as well as their specific administration days with respect to the resection surgery should be determined by a practitioner based on the type of the tumor, the severity and the overall patient's circumstances.

The subject treated by the method of the present invention is a mammal, typically a human, inflicted with cancer, including solid and non-solid tumors. Each possibility represents a separate embodiment of the invention. In some embodiments, the subject is a human inflicted with a primary solid tumor that is about to undergo tumor resection. The subject may be inflicted with any type of solid malignancy, for example, carcinomas, such as respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary, and also carcinosarcomas (e.g., which include malignant tumors composed of carcinomatous and sarcomatous tissues) and adenocarcinoma (derived from glandular tissue or in which the tumor cells form recognizable glandular structures). Additional examples of malignancies to be treated by the methods disclosed herein include sarcomas, namely malignant tumors of supportive tissues or connective tissue, for example bone or cartilage, and lymphomas, namely tumors of the lymph tissue. In certain embodiments, examples of cancer include but are not limited to, carcinoma, including adenocarcinoma, lymphoma, blastula, melanoma, and sarcoma. More particular examples of such cancers include squamous cell cancer, lung cancer (such as small-cell lung cancer, non-small cell lung cancer, lung adenocarcinoma, lung squamous cell carcinoma), gastrointestinal cancer, Hodgkin's and non-Hodgkin's lymphoma, pancreatic cancer, glioblastoma, cervical cancer, gloom, ovarian cancer, liver cancer (such as hepatic carcinoma and hematoma), bladder cancer, breast cancer, colon cancer, colorectal cancer, endometrial or uterine carcinoma, salivary gland carcinoma, kidney cancer (such as renal cell carcinoma and Wilma' tumors), basal cell carcinoma, melanoma, prostate cancer, thyroid cancer, testicular cancer, esophageal cancer, and various types of head and neck cancer.

The formation of metastasis following tumor resection can be followed up in a subject using methods known in the art, including imaging techniques, biopsies, blood tests and the like.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods

1. Animals

Four to eight months old (age varied between experiments) male and female Fischer 344 (F344) rats were housed 3-4 per cage in our vivarium at Tel Aviv University with ad-libidum access to food and water on a 12:12 light-dark cycle at 22±1° C. Animals were handled a minimum of 4 times prior to experimentation to reduce potential procedural stress. Body weight, sex, and drug administration were counterbalanced across all experimental procedures. Housing conditions were monitored by the Institutional Animal Care and Use Committee of Tel Aviv University, which also approved all studies described herein.

2. Drugs

1. GLA and its Administration

GLA (IDRI, Seattle, Wash.), dissolved in stable emulsion (SE) (2000 µg/ml) was diluted in PBS for a final concentration of 3 µg/ml-200 µg/ml (depending on the relevant experiment). One-hundred µl from the chosen concentration were injected subcutaneously (s.c.) to each animal (0.3 µg-20 µg/animal), immediately, 4 h, 12 h, 24 h, 48 h, or 96 h prior to MADB106 tumor cell inoculation (depending on the relevant experiment).

2. Stable Emulsion (SE)/Adjuvant Emulsion

SE (stable emulsion; IDRI, Seattle, Wash.) was diluted and administered in the exact manner as GLA.

3. Anti-NKR-P1

Anti-NKR-P1 is an IGg monoclonal antibody (mAb) (originally termed mAb 3.2.3) that binds to the NKR-P1 surface antigen expressed on fresh and IL-2-activated natural killer (NK) cells in rats, and, to a much lesser degree, on polymorphonuclear (PMNs) cells. In vivo treatment of rats with anti-NKR-P1 selectively depletes NK cells and eliminates NK- and antibody-dependent non-MHC-restricted cell cytotoxicity. T cell function and the percentages of T cells, peripheral blood mononuclear cells (PBMCs), and PMNs are unaffected. It has been previously shown that this antibody, but not isotype control antibodies, renders NK cells ineffective in vivo immediately upon administration, and selectively depletes NK cells within a day. The antibodies were injected i.v. under light isoflurane anesthesia simultaneously with MADB 106 tumor cell inoculation.

3. Tumor Cell Lines

1. MADB106

MADB 106 is a selected variant cell line obtained from a pulmonary metastasis of a chemically induced mammary adenocarcinoma (MADB 100) in the F344 rat. MADB 106 tumor cells metastasize only to the lungs, and lung tumor retention (LTR), which is highly indicative of the number of metastases that would have developed weeks later, is dependent upon NK cells in this model. Additionally, because the metastatic process of MADB106 is sensitive to NK activity predominantly during the first 24 h following inoculation, LTR is more reflective of in vivo NK activity levels than the number of actual metastases. The MADB 106 cell line was maintained in monolayer cultures in complete media (RPMI-1640 media supplemented with 10% heat-inactivated fetal calf serum (FCS), 50 µg/mL of gentamicin, 2 mM of l-glutamine, 0.1 mM of non-essential amino-acids, and 1 mM of sodium pyruvate, (Biological Industries, Kibbutz Biet Haemek, Israel) in 100% humidity, 5% $CO_2$ at 37° C. Cells were removed from the culture flask with trypsin solution (0.25% in PBS), and were washed with complete media. This cell line was used for both in vivo assessment of lung tumor retention and in vitro examination of NK cytotoxicity.

2. YAC-1

YAC-1 lymphoma is the standard target cell line used for the assessment of rodent in vitro NK cytotoxicity. The cell line was maintained in suspension cultures in complete media in 100% humidity, 5% $CO_2$ at 37° C.

4. Radiolabeling of MADB 106 Tumor Cells and Assessment of Lung Tumor Retention

Tumor cell DNA radiolabeling for assessment of LTR was accomplished by adding 0.5 µCi/ml of $^{125}$Iododeoxyuridine ($^{125}$IDUR, Danyel Biotech, Rehovot, Israel) to the cell culture for 24 h. For tumor cell injection, rats were lightly anesthetized with isoflurane, and $4 \times 10^5$/kg MADB106 tumor cells in 2 ml/kg PBS containing 0.1% bovine serum albumin (BSA) were injected into their tail vein. Some of the experiments also employed an additional 0.5 ml s.c. injection of epinephrine (1.8 mg/kg in females and 0.6 mg/kg in males) dissolved in a slow-release emulsion (4 parts PBS, 3 parts mineral oil (Sigma, Rehovot, Israel), and 1 part mannide-monooleate (a non-specific surface active emulsifier, Sigma, Rehovot, Israel)), for the amplification of MADB 106 retention in the lungs, allowing better group distinction. For assessment of LTR, animals were sacrificed with $CO_2$, their lungs were removed 24 h after inoculation with $^{125}$IDUR-labeled tumor cells, and placed in a γ-counter to assess percent radioactivity retained in this organ. LTR was calculated using the following formula: (radioactivity count of lung−background radioactivity)×100/(radioactivity count of the total injected cell suspension−background radioactivity).

5. EX Vivo Assessment of NK Cytotoxicity

1. Harvesting and Preparing Circulating Leukocytes, Marginating-Pulmonary (MP) Leukocytes, and Marginating-Hepatic (MH) Leukocytes for Assessment of NK Cytotoxicity Rats were sacrificed with an overdose of isoflurane and the peritoneal and chest cavities opened. Five to 8 ml of blood (females and male respectively) was collected from the right ventricle of the heart into heparinized syringes. One ml of blood was washed once with 3 ml of PBS (400 g for 10 min) and twice with 3 ml of complete medium, and reconstituted to its original volume. MP leukocytes were harvested by perfusing the heart with 30 U/ml of heparinized PBS. PBS was injected into the right ventricle and perfusate was collected from the left ventricle. The first 3 ml of perfusate, which were contaminated with blood, were discarded, and the following 25 ml were collected and concentrated to 1 ml. This was achieved by centrifuging the perfusate (400 g for 10 min), discarding the supernatant, and suspending the pellet in 3 ml of complete medium, centrifuging the perfusate again (400 g for 10 min) and concentrating the perfusate into 1 ml. MH leukocytes were similarly harvested by perfusing the liver with 30 U/ml of heparinized PBS. PBS was injected into the hepatic portal vein and perfusate was collected from the vena cava. The first 5 ml of perfusate, which were contaminated with blood, were discarded, and the following 25 ml were collected and concentrated in the same method as was described for MP leukocytes.

2. Assessment of NK Cytotoxicity

The standard whole blood $^{51}$Cr release assay was used. This procedure assesses anti-tumor NK cellular cytotoxicity (NKCC) per ml of effector cells without prior purification of the leukocyte population studied (peripheral blood mononuclear cells, MP or MH leukocytes). Earlier studies have indicated that cytotoxicity measured using this procedure is attributable to NK cells, rather than other cell types or soluble factors, as the selective depletion of NK cells abolishes all target-cell killing. The advantages of this procedure include shorter duration, less interference with the effector cells, and better representation of the original in vivo milieu of cell composition.

Six different effector to target (E:T) ratios were formed by serially diluting 150 µl aliquots of the effector-cell preparation in a microtiter plate. Then, 5000 radiolabeled target cells (MADB 106 or YAC-1) in 100 µl complete medium were added to each well on top of the effector-cell preparation. Radiolabeling of the target cells was conducted by incubating them for 1 h with 100 µCi $^{51}$Cr (Rotem Taassiot, Dimona, Israel) in 100 µl saline, 100 µl FCS, and 50 µl complete medium. Following this incubation, target cells were washed 3 times (300 g for 10 min) in complete medium and their concentration adjusted to $5 \times 10^4$/ml. Spontaneous and maximal releases of radioactivity were determined by substituting effector cells with complete medium or Triton-X100 (Sigma, Rehovot, Israel), respectively. Prior to and following a 4 h incubation period (100% humidity, 5% $CO_2$ at 37° C.) plates were centrifuged (400 g for 10 min, at 25 and 4° C., respectively). This creates a "buffy coat" of leukocytes and tumor cells on top of the red blood cells surface, enabling efficient effector-target interaction. Finally, 100 µl samples of supernatant, were recovered for the assessment of radioactivity in a γ-counter. Specific killing was calculated as: 100×[(sample release×HCF−spontaneous release)/(maximal release−spontaneous release)], Hematocrit correction factor (HCF) compensates for changes in the hematocrit-supernatant volume over different E:T ratios. This correction factor is included to consider the changing volume of cell-free medium in which the released radioactive molecules are dispersed.

6. Flow Cytometry

Standard procedures were used to prepare cells for flow cytometric analysis. NK cells in both blood, lung perfusate, and liver perfusate were identified by the APC-conjugated anti-CD161 mAb (Biolegend, San Diego, Calif.) as being $CD161^{bright}$ cells. This criterion has been shown to exclusively identify more than 95% of cells that exhibit NK activity. T cells were identified using a PE-conjugated anti-CD5 mAb (eBioscience, San Diego), and NKT cells were identified as CD161+CD5+ lymphocytes. NK activation markers were identified by the FITC-conjugated NKp46 (BiossUSA, Woburn, Mass.) and the Cy7-conjugate LAMP-1 (BiossUSA, Woburn, Mass.). Granulocytes and lymphocytes were identified based on forward and side scatters. Flow cytometry analysis was conducted using a FACScan (Becton Dickinson). To assess the absolute number of cells per µl of sample (or a specific cell subtype), 300 polystyrene microbeads (20 µm, Duke Scientific, Palo Alto) per µl sample were added to each sample, and the following formula was used: (# of cells in sample/# of microbeads in sample)×300.

7. Statistical Analyses

One- or two-way analysis of variance (ANOVA) with a pre-determined significance level of 0.05 was conducted. Provided significant group differences were found, Fisher's protected least significant differences (Fisher's PLSD) contrasts were performed to compare specific pairs of groups, based on a priori hypotheses.

Example 1

Dose Curve of the Effects of GLA on MADB106 LTR in Male Rats

The experiment was conducted in order to establish a potent dosage for GLA administration for future experiments.

Procedure:

Seventy-five three months old F344 male rats were randomly divided into one of 7 experimental groups administered with PBS, SE, or GLA in a dose/animal of 0.3 µg, 0.7 µg, 2.5 µg, 10 µg, and 20 µg. Each animal was injected s.c. with 100 µl of drug according to its group assignment, and, 24 h later, MADB 106 cells were inoculated (as detailed in section 4 above). Each of these 7 groups was further sub-divided into two separate groups—one that was injected with epinephrine during tumor inoculation, and the second that was injected with vehicle. Twenty-four hours later, animals were sacrificed and lungs were extracted for LTR assessment (as detailed in section 4).

Figure 1B:
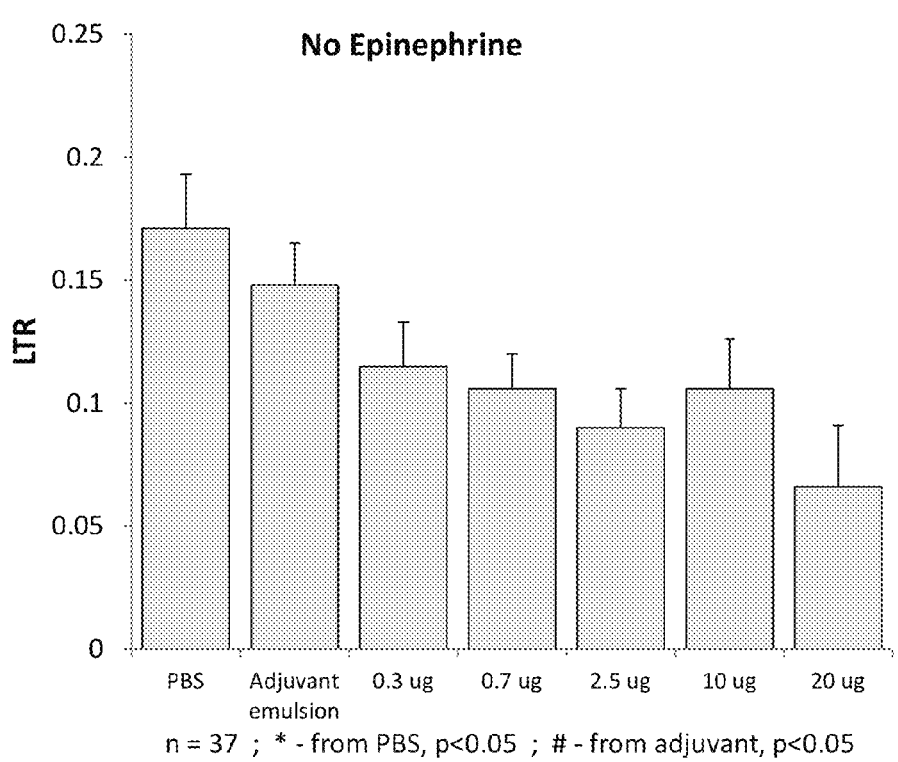

Results:

Significant main effects for treatment (SE, and GLA dose) on LTR were evident both in the epinephrine groups ($F(6, 31)=14.375$, $p<0.0001$) and in the vehicle groups ($F(6,30)=3.354$, $p<0.05$), indicating improved host ability to clear cancer cells from the lung (decreased LTR). See FIGS. 1A and 1B.

Fisher's PLSD post-hoc comparisons in the epinephrine groups indicated a significant improvement for SE over PBS ($p<0.001$), and for all GLA doses over PBS ($p<0.0001$). When examined for the additive effects of GLA over SE (due to the fact that GLA was originally dissolved in SE, which is partially responsible for its effects), significant improvements were found for the 0.7 µg, 2.5 µg, 10 µg, and 20 µg doses ($p<0.05$, $p<0.01$, $p<0.01$, and $p<0.001$, respectively).

Within the vehicle groups, Fisher's PLSD post-hoc comparisons yielded no effect for SE alone, and significant improvement for GLA over PBS in the 0.7 µg, 2.5 µg, 10 µg, and 20 µg doses ($p<0.05$, $p<0.01$, $p<0.05$, and $p<0.01$, respectively).

These results indicate a partial responsibility for the SE constituency in the beneficial effects of GLA on LTR, and an additive effect for GLA over SE effects for dosages equal or higher than 0.7 µg per animal. Following this experiment, a working dosage of 2 µg GLA per animal was determined, which enables minimal yet effective drug dose that is based on GLA-related effects beyond SE-related ones.

Also, as was already reported previously, the administration of epinephrine along with MADB 106 cell inoculation allowed better distinction between groups, by inducing a more challenging conditions to the host and increasing LTR levels. By analyzing the difference between PBS animals receiving epinephrine and those receiving vehicle, it was possible to calculate the specific epinephrine effect on LTR, and the relevant reduction effects caused by the GLA within the epinephrine groups, which positively correlated with its dosage.

Example 2

Time Course for Initiation and Duration of GLA Effects

The experiment was conducted in order to determine the duration of effect for GLA administration, and for assessing an optimal time point for its use.

Procedure:

In the first experiment, 75 six-month old F344 male rats were randomly divided into one of 5 injection time points preceding tumor inoculation—0 h, 4 h, 12 h, 24 h, and 48 h. Each group was further sub-divided into one of three experimental drug groups—PBS, SE, and 2 µg GLA. Each animal was injected s.c. with 100 µl according to its relevant drug group, in its designated time point. At time 0 h, MADB106 cells were injected (as detailed in section 4), along with epinephrine. Four additional male F344 rats were added to the PBS group and were not injected with epinephrine (received vehicle), to serve as an anchor to establish the effects of epinephrine. Twenty-four hours later, animals were sacrificed and lungs were extracted for LTR assessment (as detailed in section 4)

In the second experiment, a similar experiment was conducted in female rats. Eighty-nine six-month old F344 female rats were randomly divided into one of 6 injection time points—0 h, 4 h, 12 h, 24 h, 48 h, and 96 h. Each group was further sub-divided into one of three experimental drug groups—PBS, SE, and 2 µg GLA. All other procedures were as in males above.

Results:

In both experiments, the different time points within the PBS and SE groups showed no consistent or significant differences, and were thus combined to accumulate sufficient animal in these conditions.

Figure 2A:
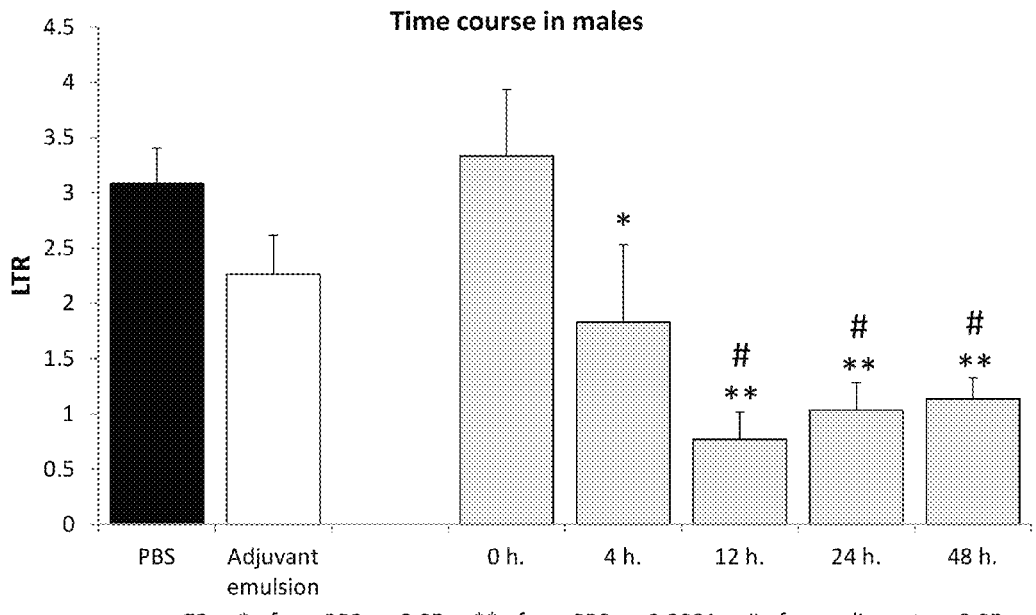
FIG. 2A and FIG. 2B: Time course for initiation and duration of GLA effects in male (FIG. 2A) and female (FIG. 2B) rats.

In the first experiment (males), significant main effect for treatment on LTR was evident ($F(7,71)=5.990$, $p<0.0001$), improving host resistance. See FIG. 2A. Fisher's PLSD post-hoc comparisons indicated no effect for SE alone, and a significant difference between GLA and PBS in time-points 4 h, 12 h, 24 h, and 48 h ($p<0.05$ for 4 h, and $p<0.0001$ for the rest).

Figure 2B:
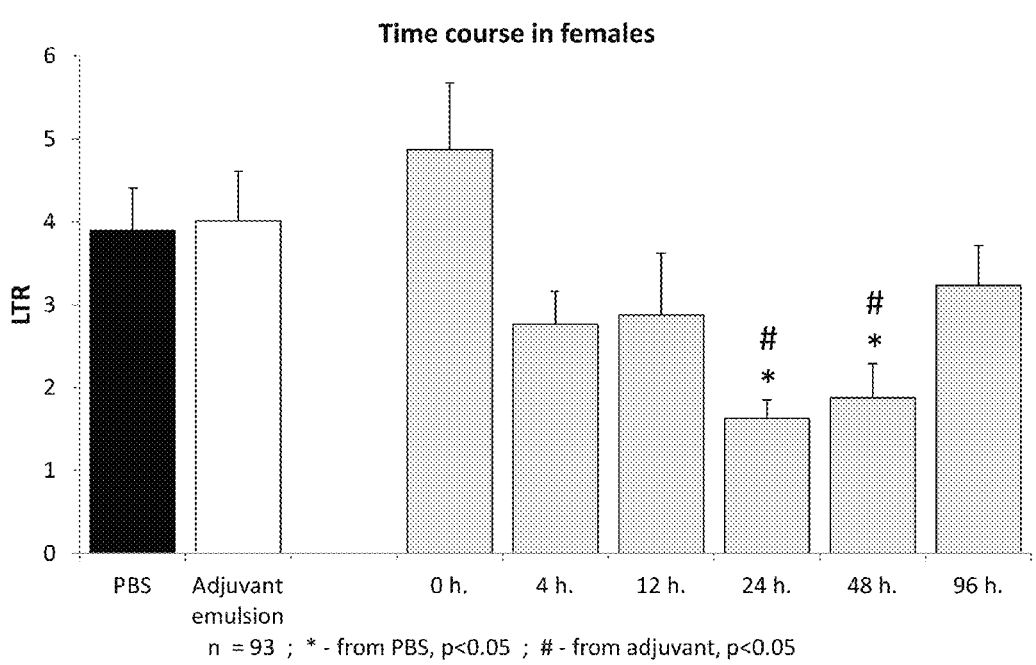

In the second experiment (females), significant main effect for treatment on LTR was evident ($F(8,84)=3.229$, $p<0.01$). See FIG. 2B. Fisher's PLSD post-hoc comparisons indicated no effect for SE alone, and a significant difference between GLA and PBS in time-points 24 h and 48 h ($p<0.05$ for both).

These results indicate a quick and a long lasting effect for a single low-dose injection of GLA in both males and females, although suggesting a better response in males to the treatment in this dose.

Example 3

A Three Week Study for the Assessment of GLA Effects on the Actual Development of MADB106 Metastases in the Lungs This experiment was conducted in order to assess in vivo effects of GLA on the actual development of cancer metastases in the lungs, rather than focusing on the shorter index of LTR.

Procedure:

Eighty-six six-month old F344 rats (44 females) were divided into three experimental groups (2 µg GLA, SE, and PBS). Each animal was injected s.c. with 100 µl according to its group assignment. Twenty-four hrs later, animals were lightly anesthetized with isoflurane and $10^5$ MADB 106 tumor cells (approximately $4 \times 10^5$/kg) were injected into their tail vein in 0.5 ml of PBS (supplemented with 0.1% BSA). Three weeks later, rats were killed, and their lungs removed and placed for 24 h in Bouin's solution (72% saturated picric acid solution, 23% formaldehyde (37% solution) and 5% glacial acetic acid). After being washed in ethanol, visible surface metastases were counted by a researcher uninformed of the origin of each lung.

Figure 3:
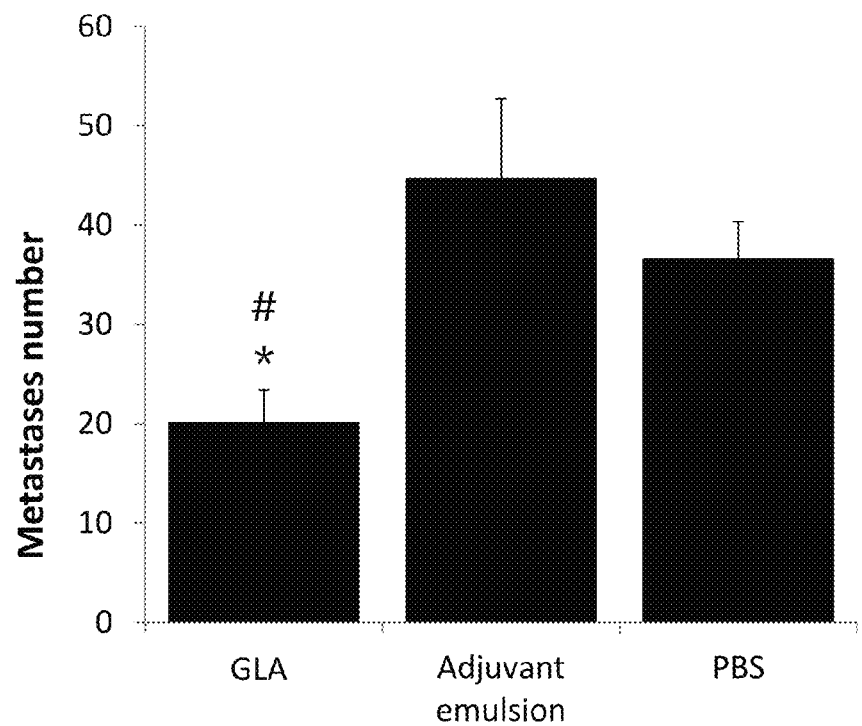
FIG. 3: GLA effects on the development of MADB 106 metastases in the lungs of rats.

Results:

Significant main effect for treatment on number of metastases was evident ($F(2,83)=5.405$, $p<0.01$). See FIG. 3.

Fisher's PLSD post-hoc comparisons indicated no effect for SE alone, and a significant difference between GLA and PBS ($p<0.05$) and between GLA and SE ($p<0.01$)—GLA reducing the number of metastases. No significant sex differences were evident.

Example 4

The Effects of GLA in Naive and in NK-Depleted Animals on MADB106 LTR

This experiment was conducted to assess the role of NK cells in mediating the beneficial impact of GLA administration on LTR.

Procedure:

Fifty-four four-month old F344 male rats were divided into two groups—NK depletion by administration of anti-NKR-P1 mAb, or vehicle administration, and each group was further sub-divided into three (2 µg GLA, SE, and PBS). Each animal was injected s.c. with 100 µl according to its drug condition assignment, and 24 h later MADB 106 cells were administered simultaneously with either the anti-NKR-P1 mAb or vehicle. Twenty-four hours later animals were sacrificed and lungs were removed for LTR assessment (as detailed in section 4).

Figure 4A:
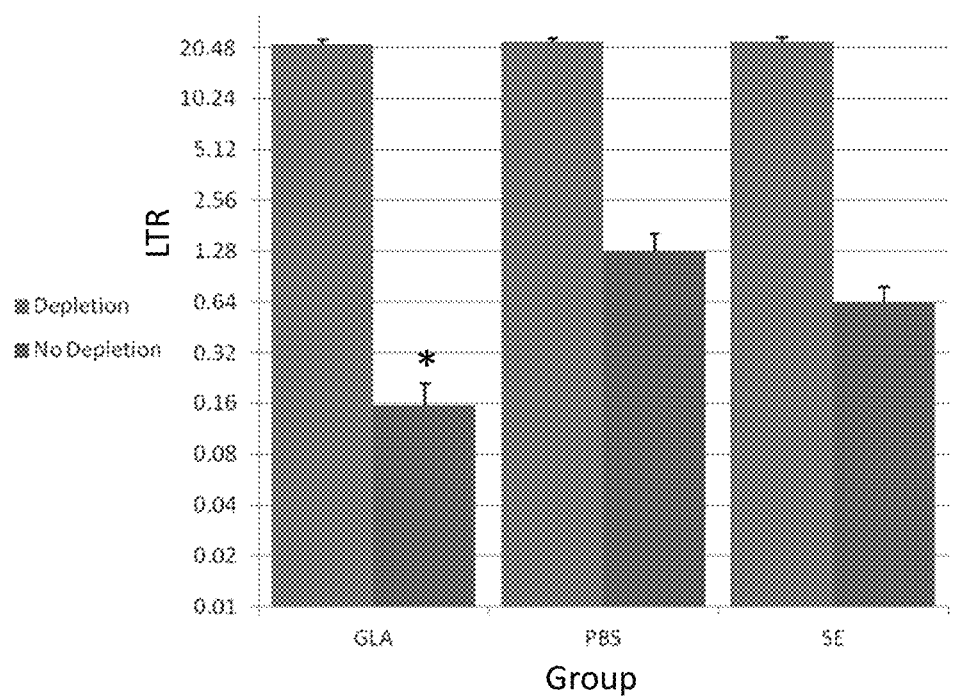
FIG. 4A and FIG. 4B: GLA effects on MADB106 LTR in naive (no-depletion) versus NK-depleted animals (FIG. 4A) and in naive (no-depletion) animals only (FIG. 4B).

Results:

A two-by-three ANOVA (depletion×drug injection) revealed a significant effect for depletion ($F(1,46)=712.065$, $p<0.0001$), showing an approximately 20-fold higher levels of LTR in NK-depleted animals, and thus the prominent role of NK cells in clearing MADB 106 from the lungs. See FIG. 4A.

Figure 4B:
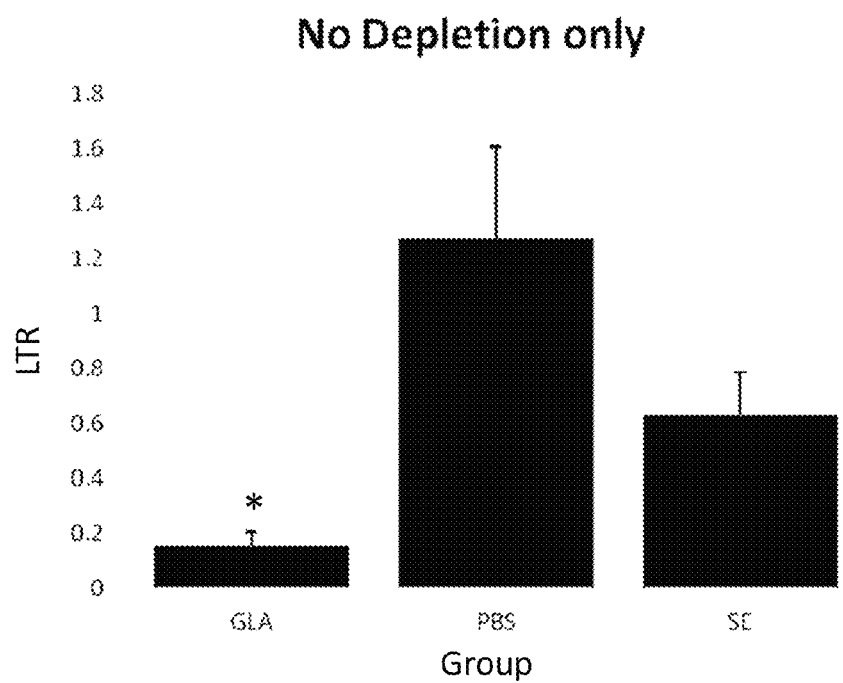

When the depletion and non-depletion groups were examined separately, no differences were evident between the depletion groups, indicating no effect for either GLA or SE under this condition, while a significant effect for group was found under the no-depletion condition ($F(2,22)=6.447$, $p<0.01$). Fisher's PLSD post-hoc comparisons for the no-depletion condition indicated no effect for SE alone, and a significant difference between GLA and PBS ($p<0.01$). See FIG. 4B. These findings indicate that the beneficial effects of GLA are mediated prominently by NK cells.

In previous studies employing this experimental approach it also shown that other manipulations increase or decrease LTR in NK-depleted animals, negating a potential methodological obstacle, such as a ceiling or flour effects, in this experimental approach.

Example 5

Testing GLA, a Beta-Blocker and a COX2 Inhibitor in Mouse Models of Spontaneous Postoperative Metastasis C57BL/6J mice are inoculated intrafootpad with syngeneic B16F10.9-melanoma or Lewis lung carcinoma, and the paw is amputated when a developing tumor exceeds 100 ml. GLA, beta-adrenergic antagonist propranolol, and/or the cyclooxygenase-2 inhibitor etodolac are administered once (or more) before amputation, and recurrence-free survival is monitored. Further experiments are conducted where GLA is administered once before amputation, and propranolol plus etodolac are administered once after amputation.

C57BL/6J male and female mice are purchased at the age of 6 wk and housed 3-4 per cage in a vivarium with ad libitum access to food and water on a 12:12 light/dark cycle at 22 6 1° C. Animals are used at the age of 10-14 wk and age-matched across all groups in each experiment. The order of tumor and drug administration is counterbalanced across all experimental groups, and control animals are injected with vehicle.

Propranolol is injected s.c. (5 mg/kg, 10 ml/kg) in an emulsion of PBS, mineral oil, and Arlacel (8:7:1). Etodolac is dissolved in corn oil and injected s.c. (50 mg/kg, 10 ml/kg). GLA is injected s.c. in a dose/animal ranging from 0.1µ-50 µg.

Each mouse is injected with $5 \times 10^4$ B16F10.9 melanoma cells or d122 Lewis lung carcinoma (in 20 ml PBS containing 0.1% BSA) intrafootpad, and tumors are visually inspected daily. Once a tumor reaches 100-150 ml in volume, the mouse is anesthetized with 2% isoflurane and undergoes a specific drug treatment, and the tumor is excised by paw amputation. Mice in which the designated tumor volume is achieved are assigned to a specific drug treatment group based on a predetermined counterbalanced order, thus ensuring equal distribution of tumor size and tumor age at excision time between the different drug groups. The experimenter conducting the amputation is unaware of the drug treatment group. Mice are subsequently monitored for morbidity signs on a daily basis for an 80 d period (and no less than 2 wk following the last morbidity incidence). Mice that show sickness behavior or manifested cancer recurrence are overdosed with isoflurane and autopsied to determine malignant foci. Sickness behavior is defined by slow body movements, irresponsiveness to environmental stimuli, significant weight loss, or tremor.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for reducing or preventing metastasis development in a subject following a tumor excision surgery, the method comprising the step of administering to the subject a pharmaceutical composition comprising glucopyranosyl lipid adjuvant (GLA) or a pharmaceutically acceptable salt thereof as an active ingredient, wherein said administration is effective in reducing or preventing metastasis, and wherein said administering is carried out during the perioperative period of said tumor excision surgery.

2. The method of claim 1, wherein said administering is by local-regional delivery.

3. The method of claim 1, wherein said pharmaceutical composition is substantially devoid of a cancer-antigen.

4. The method of claim 1, wherein said administering is carried out at least one time before the surgery (pre-operative).

5. The method of claim 1, wherein said administering is carried out at least one time after the surgery (post-operative).

6. The method of claim 1, wherein said pharmaceutic composition is administered in constant doses.

7. The method of claim 1, wherein said pharmaceutic composition is administered in varying doses.

8. The method of claim 1, wherein GLA has the following structural formula (I):

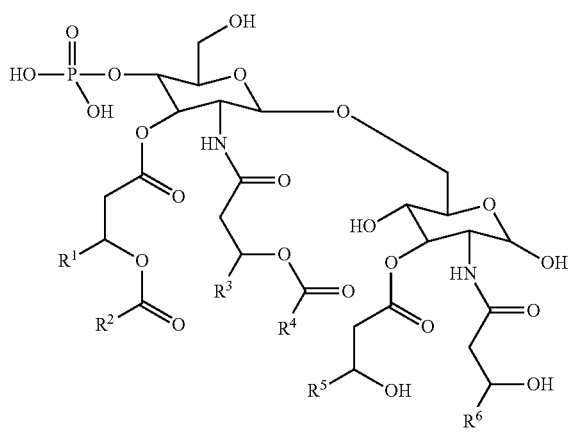

(I)

wherein:
$R^1$, $R^3$, $R^5$ and $R^6$ are $C_{11}$-$C_{20}$ alkyl; and $R^2$ and $R^4$ are $C_{12}$-$C_{20}$ alkyl.

9. The method of claim 8, wherein $R^1$, $R^3$, $R^5$ and $R^6$ are undecyl and $R^2$ and $R^4$ are tridecyl.

10. The method of claim 1, wherein GLA has the following structural formula (II):

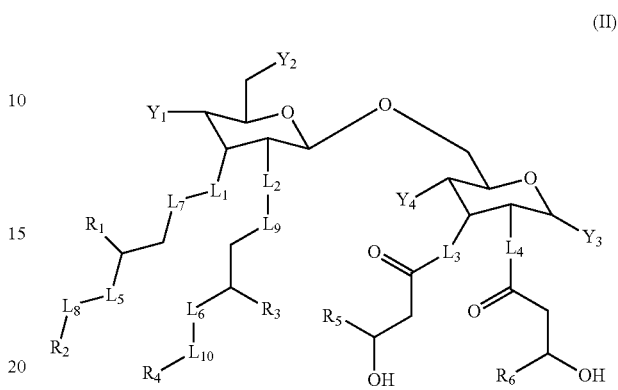

(II)

wherein:
$L_1$, $L_2$, $L_3$, $L_4$, $L_5$ and $L_6$ are the same or different and independently —O—, —NH— or —(CH$_2$)—;
$L_7$, $L_8$, $L_9$, and $L_{10}$ are the same or different and independently absent or —C(=O)—;
$Y_1$ is an acid functional group;
$Y_2$ and $Y_3$ are the same or different and independently —OH, —SH, or an acid functional group;
$Y_4$ is —OH or —SH;
$R_1$, $R_3$, $R_5$ and $R_6$ are the same or different and independently $C_8$-$C_{13}$ alkyl; and
$R_2$ and $R_4$ are the same or different and independently $C_6$-$C_{11}$ alkyl.

11. The method of claim 10, wherein GLA has the following structure:

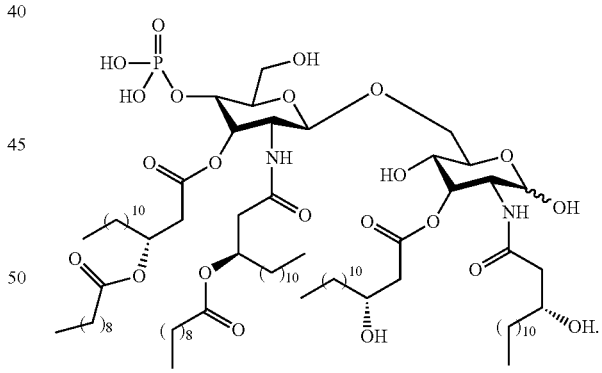

12. The method of claim 1, further comprising the step of administering a beta-adrenergic blocker, a COX2 inhibitor, or both.

13. The method of claim 12, wherein said further administering is carried out during the perioperative period of a tumor excision surgery.

14. The method of claim 12, wherein the beta-adrenergic blocker and COX2 inhibitor are present within separate pharmaceutical compositions.

15. The method of claim 13, wherein the beta-adrenergic blocker, COX2 inhibitor or both are administered at least one time before the surgery (pre-operative).

16. The method of claim 13, wherein beta-adrenergic blocker, COX2 inhibitor or both are administered at least one time after the surgery (post-operative).

17. The method of claim 13, wherein administering said pharmaceutical composition and further administering of a beta-adrenergic blocker, COX2 inhibitor, or both are carried out on the same days during the perioperative period.

18. The method of claim 13, wherein administering said pharmaceutical composition and further administering of a beta-adrenergic blocker, COX2 inhibitor, or both are carried out on separate days during the perioperative period.

19. The method of claim 12, wherein the beta-adrenergic blocker is selected from the group consisting of acebutolol, atenolol, betaxolol, bisoprolol, carteolol, carvedilol, celiprolol, esmolol, labetalol, metoprolol, nadolol, nebivolol, oxyprenolol, penbutolol, pindolol, propranolol, sotalol, timolol, and pharmaceutically acceptable salts thereof.

20. The method of claim 19, wherein the beta-adrenergic blocker is propranolol or a pharmaceutically acceptable salt thereof.

21. The method of claim 12, wherein the COX2 inhibitor is selected from the group consisting of celecoxib, cimicoxib, etoricoxib, etodolac, eoricoxib, lumiracoxib, meloxicam, parecoxib, rofecoxib, tiracoxib, valdecoxib, and pharmaceutically acceptable salts thereof.

22. The method of claim 21, wherein the COX2 inhibitor is etodolac or a pharmaceutically acceptable salt thereof.

* * * * *

UNITED STATES PATENT AND TRADEMARK OFFICE
CERTIFICATE OF CORRECTION

PATENT NO. : 9,463,198 B2
APPLICATION NO. : 14/256881
DATED : October 11, 2016
INVENTOR(S) : Shamgar Ben-Eliyahu et al.

Page 1 of 1

It is certified that error appears in the above-identified patent and that said Letters Patent is hereby corrected as shown below:

In the Claims

At Column 25, Line 40, "pharmaceutic" should be -- pharmaceutical --.

At Column 25, Line 42, "pharmaceutic" should be -- pharmaceutical --.

At Column 27, Line 7, "same days" should be -- same day --.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*